(12) United States Patent
Sangameswaran et al.

(10) Patent No.: US 8,158,682 B2
(45) Date of Patent: Apr. 17, 2012

(54) INSTILLATION ADMINISTRATION OF CAPSAICINOIDS FOR THE TREATMENT OF PAIN

(75) Inventors: Lakshmi Sangameswaran, San Jose, CA (US); Susan Kramer, San Francisco, CA (US)

(73) Assignee: Vallinex, Inc., Baltimore, MD (US)

( * ) Notice: Subject to any disclaimer, the term of this patent is extended or adjusted under 35 U.S.C. 154(b) by 338 days.

(21) Appl. No.: 12/559,071

(22) Filed: Sep. 14, 2009

(65) Prior Publication Data

US 2010/0234470 A1 Sep. 16, 2010

Related U.S. Application Data

(60) Provisional application No. 61/136,545, filed on Sep. 12, 2008.

(51) Int. Cl.
*A61K 31/166* (2006.01)
(52) U.S. Cl. .................................. 514/622; 514/818
(58) Field of Classification Search .................. None
See application file for complete search history.

(56) References Cited

U.S. PATENT DOCUMENTS

| | | | |
|---|---|---|---|
| 4,097,607 A | 6/1978 | Larson | |
| 4,313,958 A | 2/1982 | LaHann | |
| 4,532,139 A | 7/1985 | Janusz | |
| 4,536,404 A | 8/1985 | Bernstein | |
| 4,599,342 A | 7/1986 | LaHann | |
| 4,681,897 A | 7/1987 | Brand | |
| 5,431,914 A | 7/1995 | Adekunle | |
| 5,827,886 A | 10/1998 | Hersh | |
| 5,854,291 A | 12/1998 | Laughlin | |
| 5,962,532 A | 10/1999 | Campbell | |
| 6,007,538 A | 12/1999 | Levin | |
| 6,166,039 A | 12/2000 | Yaksh | |
| 6,248,788 B1 | 6/2001 | Robbins et al. | |
| 6,582,709 B1 | 6/2003 | Maor | |
| 2001/0033861 A1 | 10/2001 | Lasic | |
| 2004/0126430 A1 | 7/2004 | Angel | |
| 2005/0020690 A1* | 1/2005 | Burch et al. | |
| 2006/0269628 A1 | 11/2006 | Burch et al. | |

OTHER PUBLICATIONS

Dini, et al., "Treatment of the post-mastectomy pain syndrome with topical capsaicin", Pain, 54(2):223-26 (1993).
Kalso, et al., "Chronic post-sternotomy pain", Acta Aneasthesiologica Scandinavica, 45(8):935-39 (2001).
Menigaux, et al., "The benefits of intraoperative small-dose ketamine on postoperative pain after anterior cruciate ligament repair", Anesthesia & Analgesia 90(1):129-35 (2000).
Baron, "Capsaicin and nociception: from basic mechanisms to novel drugs", Lancet, 356(9232):785-87 (2000).
Joris, et al., "Pain after laparoscopic cholecystectomy: characteristics and effect of intraperitoneal bupivacaine", Anesthesia & Analgesia, 81(2):379-84 (1995).
Woolf and Mannion, "Neuropathic pain: aetiology, symptoms, mechanisms, and management", Lancet, 353:1959-64 (1999).
Gunter, "Surgical approaches for osteoarthritis", Best Practice & Research: Clinical Rheumatology, 15(4):627-43 (2001).
Yang and Bronson, "Cystic enlargement of the iliopsoas bursa causing venous obstruction as a complication of total hip arthroplasty. A case report.",Journal of Arthroplasty, 8(6):657-61 (1993).
Singelyn, et al., "Interscalene brachial plexus analgesia after open shoulder surgery: continuous versus patient-controlled infusion", Anesthesia & Analgesia, 89(5):1216-20 (1999).
Singelyn and Gouverneur, "Extended "three-in-one" block after total knee arthroplasty: continuous versus patient-controlled techniques", Anesthesia & Analgesia, 90(1):176-80 (2000).
Borges and Coulson, "Minimally invasive coronary bypass surgery: postoperative pain management using intermittent bupivacaine infiltration", British Journal of Anaesthesia, 80 (4):519-20 (1998).
Defalque and Bromley, "Poststernotomy neuralgia: a new pain syndrome", Anesthesia & Analgesia, 69(1):81-82 (1989).
Williams, "Curved sternotomy incision ", Texas Heart Journal, 27:419 (2000).
Furia, et al., "The efficacy and safety of the hematoma block for fracture reduction in closed, isolated fractures", Orthopedics, 20(5):423-26 (1997).
Bisgaard, et al., "Characteristics and prediction of early pain after laparoscopic cholecystectomy", Pain, 90(3):261-69 (2001) Abstract.
Aasvang, E.K. et al., "The Effect of Wound Instillation of a Novel Purified Capsaicin Formulation on Postherniotomy Pain: A Double-Blind, Randomized, Placebo-Controlled Study," *Anesth. Analg.* 107:282-291, Lippincott, Williams & Wilkins (Jul. 2008).
International Search Report for International Patent Application No. PCT/US08/10706, U.S. Patent and Trademark Office, Alexandria, Virginia, United States, mailed Dec. 3, 2008.

* cited by examiner

*Primary Examiner* — James D Anderson
*Assistant Examiner* — Gregg Polansky
(74) *Attorney, Agent, or Firm* — Pabst Patent Group LLP

(57) ABSTRACT

This present invention relates to methods for treating or attenuating pain in a patient. Specifically, the invention provides a method for attenuating pain in proximity to the site of an open wound or surgical incision comprising instilling a pharmaceutical composition comprising a capsaicinoid into the wound or incision, allowing the pharmaceutical composition to dwell for a predetermined period of time, and aspirating the wound or incision to remove the pharmaceutical composition. The invention also provides a method for attenuating pain in proximity to a joint comprising intra-articularly injecting a pharmaceutical composition comprising a capsaicinoid into the joint, allowing the pharmaceutical composition to dwell for predetermined period of time, and aspirating the joint to remove the pharmaceutical composition. In certain embodiments of the invention, the capsaicinoid is capsaicin.

27 Claims, 14 Drawing Sheets

INSTILLATION ADMINISTRATION OF CAPSAICINOIDS FOR THE TREATMENT OF PAIN

BACKGROUND OF THE INVENTION

1. Field of the Invention

This present invention relates to methods for treating or attenuating pain in a patient. Specifically, the invention provides a method for attenuating pain in proximity to the site of an open wound, arthroscopic port site, or surgical incision comprising instilling a pharmaceutical composition comprising a capsaicinoid into the wound, arthroscopic port site, or incision, allowing the pharmaceutical composition to dwell for a predetermined period of time, and aspirating the wound or incision to remove the pharmaceutical composition. The invention also provides a method for attenuating pain in proximity to a joint comprising intra-articularly injecting a pharmaceutical composition comprising a capsaicinoid into the joint, allowing the pharmaceutical composition to dwell for predetermined period of time, and aspirating the joint to remove the pharmaceutical composition. In certain embodiments of the invention, the capsaicinoid is capsaicin.

2. Related Art

Capsaicin, a pungent substance derived from the plants of the solanaceae family (hot chili peppers) has long been used as an experimental tool because of its selective action on the small diameter afferent nerve fibers C-fibers and A-delta fibers that are believed to signal pain. From studies in animals, capsaicin appears to trigger C-fiber membrane depolarization by opening cation channels permeable to calcium and sodium. Recently one of the receptors for capsaicin effects has been cloned. Capsaicin can be readily obtained by ethanol extraction of the fruit of capsicum frutescens or capsicum annum. Capsaicin is known by the chemical name N-(4-hydroxy-3-methoxybenzyl)-8-methylnon-trans-6-enamide. Capsaicin is practically insoluble in water, but freely soluble in alcohol, ether, benzene and chloroform. Therapeutically capsaicin has been used as a topical analgesic. Capsaicin is available commercially as Capsaicin USP from Steve Weiss & Co., 315 East $68^{th}$ Street, New York, N.Y. 10021 and can also be prepared synthetically by published methods. See Michalska et al., "Synthesis and Local Anesthetic Properties of N-substituted 3,4-Dimethoxyphenethylamine Derivatives," *Diss Pharm. Pharmacol.*, 24:17-25: (1972) (Chem. Abs. 77: 19271a), discloses N-pentyl and N-hexyl 3,4-dimethoxyphenylacetamides which are reduced to the respective secondary amines.

Capsaicin is listed in the pharmacopoeias of the United Kingdom, Australia, Belgium, Egypt, Germany, Hungary, Italy, Japan, Poland, Portugal, Spain, and Switzerland and has previously been listed in the United States Pharmacopoeia and the National Formulary. The FDA proposed monographs on analgesic drug products for over-the-counter (OTC) human use. These include capsaicin and capsicum preparations that are regarded as safe and effective for use as OTC external analgesics. Capsaicin is the only chemical entity of Capsicum recognized by the FDA. Capsaicin (USP) contains not more than 110% total capsaicinoids which typically corresponds to 63% pure capsaicin. USP capsaicin is trans-capsaicin (55-60%) and also contains the precursors dihydrocapsaicin and nordihydrocapsaicin.

Reported capsaicin mediated effects include: (i) activation of nociceptors in peripheral tissues; (ii) eventual desensitization of peripheral nociceptors to one or more stimulus modalities; (iii) cellular degeneration of sensitive A-delta and C-fiber afferents; (iv) activation of neuronal proteases; (v) blockage of axonal transport; and (vi) the decrease of the absolute number of nociceptive fibers without affecting the number of non-nociceptive fibers.

The dosage forms of capsaicin which have been most widely studied clinically are capsaicin containing creams (Zostrix, Zostrix-HP, and Axsain). These products have been examined in a broad spectrum of painful conditions including osteoarthritis. However the efficacy of topically administered capsaicin in arthritis in general has proven to be limited.

Prior publications describe topical administration of capsaicin for the treatment of various conditions. For example, U.S. Pat. No. 4,997,853 (Bernstein) describes methods and compositions utilizing capsaicin as an external analgesic. U.S. Pat. No. 5,063,060 (Bernstein) describes compositions and methods for treating painful, inflammatory or allergic disorders. U.S. Pat. No. 5,178,879 (Adekunle, et al.) describes methods for preparing a non-greasy capsaicin gel for topical administration for the treatment of pain. U.S. Pat. No. 5,296,225 (Adekunle, et al.) describes indirect methods of treating orofacial pain with topical capsaicin. U.S. Pat. No. 5,665,378 (Davis, et al.) describes transdermal therapeutic formulations comprising capsaicin, a nonsteroidal anti-inflammatory agent and pamabrom for the treatment of pain. U.S. Pat. No. 6,248,788 (Robbins, et al.) describes administration of 7.5% capsaicin cream in combination with marcaine epidural injections in patients suffering from long-term persistent foot pain. U.S. Pat. No. 6,239,180 (Robbins) describes combining capsaicin loaded patches with local anesthesia to treat peripheral neuropathy. The use of topical capsaicin has also been described in the art to treat conditions as diverse as post mastectomy pain syndrome (Watson and Evans, *Pain* 51:375-79 (1992)); painful diabetic neuropathy (Tandan et al., *Diabetes Care* 15:8-13 (1992)); The Capsaicin Study Group, *Arch Intern Med* 151:2225-9 (1991); post-herpetic neuralgia (Watson et al., *Pain* 33:333-40 (1988)), Watson et al., *Clin. Ther.* 15:510-26 (1993); Bernstein et al., *J. Am. Acad Dermatol* 21:265-70 (1989) and pain in Guillian-Barre syndrome (Morganlander et al., *Annals of Neurology* 29:199 (1990)). Capsaicin has also been used in the treatment of osteoarthritis (Deal et al., *Clin Ther* 13:383-95 (1991); McCarthy and McCarthy, *J. Rheumatol* 19: 604-7 (1992); Altman et al., *Seminars in Arthritis and Rheumatism* 23:25-33 (1994). In addition, U.S. Pat. No. 4,599,342 (LaHann) describes oral and subcutaneous or intramuscular administration of a combination of capsaicin or a capsaicin analog with an opioid analgesic. U.S. Pat. No. 4,313,958 (LaHann) describes intrathecal, epidural, intramuscular, intravenous, intraperitoneal and subcutaneous administration of capsaicin utilizing a "stair-step" dosing pattern.

Because of capsaicin's ability to desensitize nociceptors in peripheral tissues, its potential analgesic effects have also been assessed in various clinical trials. However, since the application of capsaicin itself frequently causes localized burning pain and hyperalgesia apart from the neuropathic pain being treated, patient compliance has been poor and the drop out rates during clinical trials have exceeded fifty percent. The spontaneous burning pain and hyperalgesia are believed to be due to intense activation and temporary sensitization of the peripheral nociceptors at the site of capsaicin application. This activation and sensitization occur prior to the desensitization phase. The activation phase could be a barrier to use of capsaicin because of the pain produced. (Winter et al., *British Journal of Anaethesia* 75:157-168 (1995)).

Beyond local side effects at the site of capsaicin administration, such as burning pain and hyperalgesia, systemic side effects of capsaicin administration may include hypothermia (Winter et al., British Journal of Anaethesia 75:157-168 (1995) and Gharat and Szallasi, Drug Development Research 68:477-497 (2007)); bronchoconstriction (Wrigglesworth et al., J Med Chem 39:4942-4951 (1996)), silent myocardial infarction (Gharat and Szallasi, Drug Development Research 68:477-497 (2007)), and gastric toxicity (referred gastric pain) (Petruzzi et al., J Oral Pathol Med 33:111-114 (2004)).

Thus, there exists a need to develop methods of administering capsaicin and other capsaicinoids in therapeutically effective concentrations that do not cause unwanted side-effects normally associated with the use of capsaicin.

SUMMARY OF THE INVENTION

The present invention is based in part on the discovery that a pharmaceutical composition comprising a capsaicinoid can be instilled into an open wound or surgical incision, allowed to dwell for a period of time, and removed via aspiration to provide sustained analgesic effects. Such a method minimizes or avoids any potential unwanted side-effects associated with systemic exposure to a capsaicinoid. Thus, in one embodiment, the invention provides a method for attenuating pain in proximity to an open wound or surgical incision in a patient comprising:

(a) instilling a therapeutically effective amount of a pharmaceutical composition comprising a capsaicinoid into said open wound, arthroscopic port site, or surgical incision;

(b) allowing said pharmaceutical composition to dwell for about 2 minutes to about 10 minutes; and (c) aspirating said open wound, arthroscopic port site, or surgical incision to remove said pharmaceutical composition.

In a further embodiment, the invention provides a method for attenuating pain in proximity to a surgical incision in a patient comprising:

(a) instilling a pharmaceutical composition comprising about 1000 µg to about 15,000 µg of purified capsaicin into said surgical incision;

(b) allowing said pharmaceutical composition to dwell for about 2 minutes to about 10 minutes; and (c) aspirating said surgical incision to remove said pharmaceutical composition.

In another embodiment, the invention provides a method for attenuating pain in proximity to a joint in a patient comprising:

(a) intra-articularly injecting a therapeutically effective amount of a pharmaceutical composition comprising a capsaicinoid into said joint;

(b) allowing said pharmaceutical composition to dwell for about 2 minutes to about 10 minutes; and (c) aspirating said joint to remove said pharmaceutical composition.

In a further embodiment, the invention provides a method of attenuating pain in proximity to a knee joint in a patient comprising:

(a) intra-articularly injecting a pharmaceutical composition comprising about 100 to about 1000 µg of purified capsaicin into said knee joint;

(b) allowing said pharmaceutical composition to dwell for about 2 minutes to about 10 minutes; and (c) aspirating said knee joint to remove said pharmaceutical composition.

Other features and advantages of the invention will be apparent from the following detailed description, and from the claims. The disclosed materials, methods, and examples are for illustrative purposes only and are not intended to be limiting. Skilled artisans will appreciate that methods and materials similar or equivalent to those described herein can be used to practice the invention.

Unless otherwise defined, all technical and scientific terms used herein have the meaning commonly understood by one skilled in the art to which this invention belongs. In case of conflict, the present specification, including definitions, will control.

DETAILED DESCRIPTION OF THE INVENTION

Capsaicinoids

Figure 1:
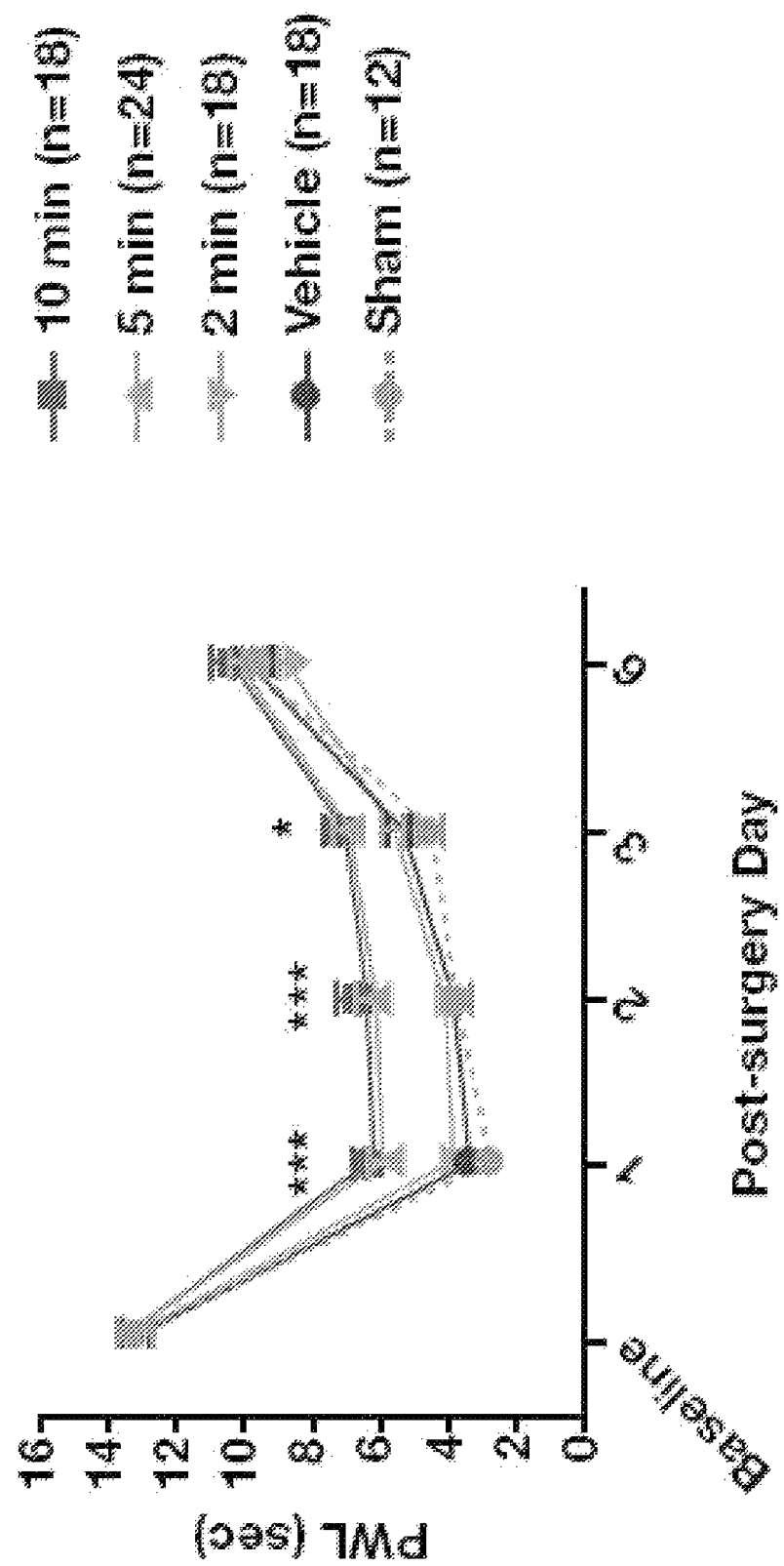
FIG. 1 is a line graph showing that intraoperative instillation of capsaicin reduces postsurgical thermal hyperalgesia in a rat paw incision model (PWL=paw withdrawal latency).

The methods disclosed herein can be used for treating or attenuating pain in proximity to an open wound, arthroscopic port site, or surgical incision via instillation of a therapeutically effective amount of a pharmaceutical composition comprising a capsaicinoid.

The term "capsaicinoid" as used herein refers to capsaicin, capsaicin analogs, and other chemical substances having similar physiological properties to capsaicin (e.g., triggering C fiber membrane depolarization by opening of cation channels permeable to calcium and sodium). Resiniferatoxin is described as a capsaicin analogue in U.S. Pat. No. 5,290,816 to Blumberg. U.S. Pat. No. 4,812,446 to Brand (Procter & Gamble Co.) describes other capsaicin analogues and methods for their preparation. U.S. Pat. No. 4,424,205 describes capsaicin analogues. Ton et al., *Brit. J. Pharm.* 10:175-182 (1955) describes the pharmacological actions of capsaicin and its analogues. Capsaicin, capsaicin analogues and other capsaicinoids are also described in detail in WO 96/40079. Capsaicinoids are also described in EPO 149 545.

Exemplary capsaciniods include, but are not limited to, N-vanillylnonanamides, N-vanillylsulfonamides, N-vanillylureas, N-vanillylcarbamates, N[(substituted phenyl)methyl] alkylamides, methylene substituted N[(substituted phenyl) methyl]alkanamides, N[(substituted phenyl)methyl]-cis-monosaturated alkenamides, N[(substituted phenyl)methyl] diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamde, nonivamide, olvanil, N-oleyl-homovanillamidia, isovelleral, scalaradial, ancistrodial, β-acaridial, merulidial, and scutigeral, and any combinations or mixtures thereof.

In certain embodiments of the invention, the capsaicinoid is selected from the group consisting of resiniferatoxin, capsaicin, and purified capsaicin.

The term "purified capsaicin" as used herein refers to capsaicin consisting essentially of trans-capsaicin, e.g., having a purity of greater than about 97%, e.g, greater than about 98%, and e.g., greater than about 99% trans-capsaicin. The trans-isomer of capsaicin has its activity at the vanilloid receptor, and is especially useful for treating disorders or pain that can be alleviated through activation of the vanilloid receptors via the VR-1 mechanism. By way of comparison, Capsaicin USP contains only about 55-60% trans-capsaicin, with the remainder comprising the precursors dihydrocapsaicin and nordihydrocapsaicin. Purified capsaicin can be prepared in accordance with the methods described in U.S. Patent Publication Nos. 2005/0019436 A1 and 2006/0269628 A1.

In certain embodiments of the invention, the therapeutically effective amount of a capsaicinoid (e.g. the amount of capsaicinoid effective to denervate an open wound or surgical incision) is from about 1 µg to about 15,000 µg, e.g., about 10 µg, about 20 µg, about 30 µg, about 40 µg, about 50 µg, about 100 µg, about 200 µg, about 300 µg, about 500 µg, about 400 µg, about 500 µg, about 600 µg, about 700 µg, about 800 µg, about 900 µg, about 1000 µg, about 2000 µg, about 3000 µg, about 4000 µg, about 5000 µg, about 6000 µg, about 7000 µg, about 8000 µg, about 9000 µg, about 10,000 µg, about 11,000 µg, about 12,000 µg, about 13,000 µg, or about 14,000 µg.

In certain embodiments, the effective dose of capsaicinoid is from about 500 µg to about 15,000 µg, or from about 600 µg to about 10,000 µg, e.g., about 600 µg, about 700 µg, about 800 µg, about 900 µg, about 1000 µg, about 2000 µg, about 3000 µg, about 4000 µg, about 5000 µg, about 6000 µg, about 7000 µg, 8000 µg, or 9000 µg, of capsaicin, or a therapeutically equivalent dose of a capsaicinoid other than capsaicin.

The volume of a pharmaceutical composition comprising a capsaicinoid that is to be administered to the patient will depend on the surgical site, size of the open wound, surgical anatomic space, or the size and type of the joint being treated. Thus, in certain embodiments, the dose of capsaicinoid is administered in a pharmaceutically acceptable carrier for instillation or intra-articular injection in a volume from about 0.1 to about 1000 ml, e.g., about 1 ml, about 5 ml, about 10 ml, about 50 ml, about 100 ml, about 250 ml, about 500 ml, or about 750 ml, depending on the site, wound opening, or surgical anatomic space to be treated. In another embodiment, the dose capsaicinoid is administered in a pharmaceutically acceptable carrier for instillation or intra-articular injection in a volume from about 1 ml to about 100 ml, e.g., about 10 ml, about 20 ml, about 30 ml, about 40 ml, about 50 ml, about 60 ml, about 70 ml, about 80 ml, or about 90 ml. In a particular embodiment, the dose of capsaicin is administered in a pharmaceutically acceptable carrier for instillation in a volume of from about 4 ml to about 60 ml. In another particular embodiment, the dose of capsaicin is administered in a pharmaceutically acceptable carrier for intra-articular injection in a volume of from about 1 ml to about 5 ml.

Pharmaceutical Formulations

In the methods of the present invention, a pharmaceutical composition comprising a capsaicinoid can be administered by instillation into a surgical incision, surgical anatomic space, or wound opening (e.g., tissue, muscle, and bone), or by intra-articular injection into a joint with any instrument known to those skilled in the art for administering agents via instillation or intra-articular injection, e.g., a needle, arthroscopic port or syringe, or any combination thereof.

The dose of capsaicinoid is prepared for instillation or intra-articular injection by being incorporated into a pharmaceutically and physiologically acceptable carrier (vehicle). For example, the capsaicinoid may be dissolved in oils, propyleneglycol or other solvents commonly used to prepare instillable solutions. Suitable pharmaceutically acceptable vehicles include aqueous vehicles, nonaqueous vehicles, antimicrobial agents, isotonic agents, buffers, antioxidants, suspending and dispersing agents, emulsifying agents, sequestering or chelating agents and any combinations or mixtures thereof. Examples of aqueous vehicles include Sodium Chloride Injection, Bacteriostatic Sodium Chloride Injection, Ringers Injection, Isotonic Dextrose Injection, Sterile Water Injection, Bacteriostatic Sterile Water Injection, Dextrose Lactated Ringers Injection and any combinations or mixtures thereof. Nonaqueous parenteral vehicles include fixed oils of vegetable origin, cottonseed oil, corn oil, sesame oil, peanut oil and any combinations or mixtures thereof. Antimicrobial agents in bacteriostatic or fungistatic concentrations include phenols, cresols, mercurials, benzyl alcohol, chlorobutanol, ethyl and propyl p-hydroxybenzoic acid esters, thimerosal, benzalkonium chloride benzethonium chloride and mixtures thereof. Isotonic agents include sodium chloride, dextrose and any combinations or mixtures thereof. Buffers include acetate, phosphate, citrate and any combinations or mixtures thereof. Antioxidants include ascorbic acid, sodium bisulfate and any combinations or mixtures thereof. Suspending and dispersing agents include sodium carboxymethylcelluose, hydroxypropyl methylcellulose, polyvinylpyrrolidone and any combinations or mixtures thereof. Emulsifying agents include Polysorbate 80 (Tween 80). Sequestering or chelating agents of metal ions include ethylenediaminetetraacetic acid. Additional pharmaceutically acceptable vehicles also include ethyl alcohol, polyethylene glycol, glycerin and propylene glycol for water miscible vehicles and sodium hydroxide, hydrochloric acid, citric acid or lactic acid for pH adjustment and any combinations or mixtures thereof.

Depending on the pharmaceutically acceptable vehicle chosen, the dose of capsaicinoid can be administered as an aqueous solution or suspension for instillation or intra-articular injection (see: H. C. Ansel, Introduction to Pharmaceutical Dosage Forms, 4th Edit., 1985, pg. 238).

In certain other embodiments, a surfactant can be combined with one or more of the pharmaceutically acceptable vehicles previously described herein so that the surfactant or buffering agent prevents the initial stinging or burning discomfort associated with capsaicinoid administration, as a wetting agent, emulsifier, solubilizer and/or antimicrobial.

Suitable surfactants include, but are not limited to, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations thereof. When one or more surfactants are utilized in the formulations of the invention, they may be combined, e.g., with a pharmaceutically acceptable vehicle and may be present in the final formulation, e.g., in an amount ranging from about 0.1% to about 20%, and e.g, from about 0.5% to about 10%.

Buffering agents may also be used to provide drug stability; to control the therapeutic activity of the drug substance (Ansel, Howard C., "Introduction to Pharmaceutical Dosage Forms," $4^{th}$ Ed., 1985); and/or to prevent the initial stinging or burning discomfort associated with capsaicin administration. Suitable buffers include, but are not limited to sodium bicarbonate, sodium citrate, citric acid, sodium phosphate, pharmaceutically acceptable salts thereof and combinations thereof. When one or more buffers are utilized in the formulations of the invention, they may be combined, e.g., with a pharmaceutically acceptable vehicle and may be present in the final formulation, e.g., in an amount ranging from about 0.1% to about 20%, and e.g., from about 0.5% to about 10%.

In certain embodiments, the pharmaceutical vehicle utilized to deliver the capsaicinoid formulation (i.e., the pharmaceutical composition comprising the capsaicinoid) comprises polyethylene glycol (PEG), histidine, and sucrose, in water for injection. In other embodiments, the pharmaceutical vehicle utilized to deliver the capsaicinoid formulation comprises about 20% PEG 300, about 10 mM histidine and about 5% sucrose, in water for injection. In a particular embodiment, the pharmaceutical vehicle utilized to deliver the capsaicinoid formulation is 25% PEG 300 in water.

In other embodiments, delivery systems can be used to administer a unit dose of capsaicinoid. The dose of capsaicinoid can be administered as microparticles (microcapsules or microspheres). The microparticles are in a size and distribution range suitable for instillation. The diameter and shape of the microparticles can be manipulated to modify the release characteristics. For example, larger diameter microparticles will typically provide slower rates of release and reduced tissue penetration and smaller diameters of microparticles will produce the opposite effects, relative to microparticles of different mean diameter, but of the same composition. In addition, other particle shapes, such as cylindrical shapes, can also modify release rates by virtue of the increased ratio of surface area to mass inherent to such alternative geometrical shapes, relative to a spherical shape. The diameter of microparticles range in size from about 5 microns to about 200 microns in diameter.

In a further embodiment, the microparticles range in diameter from about 20 to about 120 microns. Methods for manufacture of microparticles are well known in the art and include solvent evaporation, phase separation and fluidized bed coating.

DEFINITIONS

The term "instillation" as used herein refers to drop by drop administration of a pharmaceutical composition into a discrete surgical site (e.g., an incision) or open wound of a patient.

The term "intra-articular" as used herein refers to within the cavity of a joint.

Patients which may be treated with capsaicinoids according to the methods of present invention include mammals, e.g., humans, although the invention is not intended to be so limited. Other patients include veterinary animals (cows, sheep, pigs, horses, dogs, cats and the like).

The term "about" as used herein refers to the recited number+/−10%. Thus, "about 0.5" means 0.45 to 0.55.

The term "proximity" as used herein refers to being near or next to, for example, 1.25 centimeters from the local treatment area.

The term "aspirating" or "aspiration" as used herein refers to removing a pharmaceutical composition from a surgical incision site, open wound, or joint cavity. Aspiration techniques are well known to the clinical practitioner of ordinary skill. In the context of the present invention, aspiration of the surgical incision site, open wound, or joint cavity substantially removes the pharmaceutical composition comprising the capsaicinoid administered by instillation or intra-articular injection, although small amounts of the capsaicinoid will remain.

The term "analgesia" as used herein refers to a reduction or absence of the perception of pain.

The term "acute pain" as used herein refers to any pain that presents with a rapid onset followed by a short, severe course, e.g., headache, pain associated with cancer, fractures, strains, sprains, and dislocations of bones, joints, ligaments and tendons.

The term "chronic pain" as used herein refers to any pain that lasts for a long period of time or is marked by frequent recurrence, e.g., pain associated with terminal illnesses, arthritis, autoimmune diseases; or neuropathic pain caused by degenerative diseases such as diabetes mellitus or spinal degeneration, or resulting from neural remodeling following traumatic injury or surgery.

The term "local anesthetic" or "local anesthetic agent" as used herein refers any drug or mixture of drugs that provides local numbness and/or analgesia.

In certain embodiments, the methods involve providing anesthesia to the surgical site or open wound where the pharmaceutical composition comprising the capsaicinoid is to be administered, and then administering an effective amount of pharmaceutical composition to the surgical site or open wound. The anesthesia can be provided directly to the surgical site or open wound, or at a remote site that causes anesthesia at the surgical site or open wound where the capsaicinoid is to be administered. General anesthesia may also be used. Epidural regional anesthesia can be provided to patients to which the capsaicinoid is to be administered at a surgical site or open wound located from the waist down. Alternatively, a local anesthetic may be administered as a regional block, a proximal block, a somatic block, or a neuraxial block. The anesthetic may be administered as a general anesthetic, as a spinal block, as an epidural block, or as a nerve block. In the embodiments in which a local anesthetic is administered, the local anesthetic is administered prior to administration of the capsaicinoid, such that the local anesthetic has provided temporary anesthesia to the area to be treated with the capsaicinoid.

Exemplary non-limiting examples of local anesthetic agents which can be used in the methods of the present invention include bupivacaine, ropivacaine, dibucaine, procaine, chloroprocaine, prilocalne, mepivacaine, etidocaine, tetracaine, lidocaine, and xylocalne, and mixtures thereo, and any other art-known pharmaceutically acceptable local anesthetic. The local anesthetic can be in the form of a salt, for example, the hydrochloride, bromide, acetate, citrate, carbonate or sulfate salt. Or the local anesthetic agent can be in the form of a free base such as bupivacaine. For bupivacaine, the free base provides a slower initial release and avoids an early "dumping" of the local anesthetic at the infiltration site. Other local anesthetics may act differently. Local anesthetic agents typically administered systematically may also be used in those cases where the means of administration results only in a local effect, rather than systemic.

In a particular embodiment of the invention, the local anesthetic is lidocaine

The dose of local anesthetic will depend on the anesthetic being administered as well as the site where the local anesthetic is administered. For example, in embodiments where the local anesthetic is administered via a regional block (e.g., an ankle block), the dose of anesthetic ranges from about 1 ml up to about 30 ml of a 0.5% solution (e.g., bupivacaine). In other embodiments a 3 mg/kg dose (maximum 200 mg) of a 2% solution (e.g., lidocaine) can be administered by intraarticular infiltration. In other embodiments the dose of local anesthetic can range between 0.5 ml to about 60 ml of a 0.25% to 5% solution.

Alternatively, phenol can be administered at the surgical incision or open wound to be treated in place of (or in addition to) a local anesthetic to anesthesize the area. Phenol can be administered prior to administration of the capsaicinoid, or can be co-administered with the dose of capsaicinoid.

The term "co-administration" as used herein refers to either the administration of a single composition containing both the capsaicinoid and an additional therapeutically effective agent(s), e.g., local anesthetic or phenol, or the administration of a capsaicinoid and the additional therapeutically effective agent(s) as separate compositions within short enough time periods that the effective result is equivalent to that obtained when both compounds are administered as a single composition.

The local anesthetic can be administered by direct injection or implantation to the site where the capsaicinoid formulation is to be administered, for example, by administering the local anesthetic directly into the surgical incision or open wound or to the nerve that provides inervation to the area surrounding the incision or open would, or to effect a regional block of the area.

The local anesthetic can also be administered by injection or implantation into the epidural space adjacent to the spine for pain originating below a patient's waist, or directly into a joint for pain originating above the patient's waist. The prior administration of a proximal neural block sufficiently desensitizes C fibers to the expected pungent side effects of the subsequent capsaicin administration.

In an embodiment wherein the anesthetic is administered as microspheres, the microspheres may be injected, implanted or infiltrated through a trochar, or the pellets or slabs may be surgically placed adjacent to nerves, prior to surgery or following repair or washing of a wound. The microspheres can be administered alone when they include both the capsaicin and local anesthetic or in combination with a solution including capsaicin in an amount effective to prolong nerve blockade by the anesthetic released from the microspheres. The suspensions, pastes, beads, and microparticles will typically include a pharmaceutically acceptable liquid carrier for administration to a patient, for example, sterile saline, sterile water, phosphate buffered saline, or other common carriers.

The term "pharmaceutically acceptable carrier" or "pharmaceutically acceptable vehicle" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences, Mack Publishing Co., Easton, Pa., 19th ed. 1995.

The term "breakthrough pain" as used herein refers to pain that the patient experiences despite the fact that the patient is being or was administered generally effective amounts of, e.g., capsaicin. In conjunction with the use of the capsaicinoid formulations and methods described herein, it is contemplated that it is nonetheless possible that the patient will experience breakthrough pain. For the treatment of breakthrough pain, the individual may be further administered an effective amount of an analgesic in accordance with the treatment of pain in such situations performed by those skilled in the art. The analgesic may be any known to the person skilled in the art such as those selected from the group comprising gold compounds such as sodium aurothiomalate; non-steroidal anti-inflammatory drugs (NSAIDs) such as naproxen, diclofenac, flurbiprofen, ibuprofen ketoprofen, ketorolac, pharmaceutically acceptable salts thereof and the like; opioid analgesics such as codeine, dextropropoxyphene, dihydrocodeine, morphine, diamorphine, hydromorphone, hydrocodone, methadone, pethidine, oxycodone, levorphanol, fentanyl and alfentanil, para-aminophenol derivatives such as paracetamol, pharmaceutically acceptable salts thereof and the like; and salicylates such as aspirin.

The expected side effects of the instillation administration of a pharmaceutical composition comprising capsaicin are believed to be from the intense nociceptor discharge occurring during the excitatory phase before nociceptor desensitization. However, the prior administration of an anesthetic, such as a nerve block, proximally or directly to the site of administration, eliminates or substantially reduces such side effects. Capsaicin pain on administration is transient, short duration, e.g. minute to a few hours, and dose-related. If some "breakthrough pain" occurs despite the anesthetic, this pain may be treated by administering an analgesic such as a nonsteroidal anti-inflammatory agent or narcotic analgesic (i.e., the various alkaloids of opium, such as morphine, morphine salts, and morphine analogues such as normorphine). The administration of the capsaicin can be repeated if necessary.

METHODS OF THE INVENTION

In one aspect, the present invention provides methods for treating or attenuating pain in proximity to an open wound, arthroscopic port, surgical incision in a patient comprising:

a) instilling a therapeutically effective amount of a pharmaceutical composition comprising a capsaicinoid into said open wound, arthroscopic port, or surgical incision;

(b) allowing said pharmaceutical composition to dwell for about 2 minutes to about 10 minutes; and (c) aspirating said open wound, arthroscopic port, or surgical incision to remove said pharmaceutical composition.

In certain embodiments, the invention provides methods for treating or attenuating nociceptive pain, i.e., pain transmitted across intact neuronal pathways. Nociceptive pain includes, but is not limited to post-operative pain, cluster headaches, dental pain, surgical pain, pain resulting from severe burns, postpartum pain, angina, genitor-urinary tract pain, pain associated with sports injuries (tendonitis, bursitis, etc) and pain associated with joint degeneration and cystitis. In particular embodiments, the invention provides methods for treating or attenuating post-operative pain and surgical pain.

In another aspect, the present invention provides methods for treating or attenuating pain in proximity to an open wound, arthroscopic port, or surgical incision in a patient comprising:

(a) instilling a therapeutically effective amount of a pharmaceutical composition comprising a capsaicinoid into said open wound, arthroscopic port, or surgical incision;

(b) allowing said pharmaceutical composition to dwell for about 2 minutes to about 10 minutes;

(c) aspirating said open wound, arthroscopic port, or surgical incision to remove said pharmaceutical composition; and (d) closing said open wound or surgical incision.

In certain embodiments, the incision or wound is closed using sutures. Surgical techniques used to close incisions and open wounds are well known to the clinical practitioner of ordinary skill.

In another embodiment, the invention provides a method for attenuating pain in proximity to a joint in a patient comprising:

(a) intra-articularly injecting a therapeutically effective amount of a pharmaceutical composition comprising a capsaicinoid into said joint;

(b) allowing said pharmaceutical composition to dwell for about 2 minutes to about 10 minutes; and (c) aspirating said joint to remove said pharmaceutical composition.

In certain embodiments, the pharmaceutical composition is allowed to dwell for about 2 minutes, about 3 minutes, about 4 minutes, about 5 minutes, about 6 minutes, about 7 minutes, about 8 minutes, about 9 minutes, or about 10 minutes.

In certain embodiments, the methods of the present invention further comprise co-administering one or more additional therapeutic agents to said patient.

In certain embodiments, a local anesthetic is administered to the patient, wherein the local anesthetic is administered prior to or concurrently with said capsaicinoid in an amount and location effective to attenuate an initial hyperalgesic effect of said administered capsaicinoid. In a particular embodiment, the local anesthetic is selected from the group consisting of dibucaine, bupivacaine, ropivacaine, etidocaine, tetracaine, procaine, chlorocaine, prilocalne, mepivacaine, lidocaine, xylocalne, 2-chloroprocaine, and acid addition salts or mixtures thereof. In certain embodiments, the local anesthetic is administered by infiltration in proximity to said open wound or surgical incision.

In certain embodiments, the methods of the present invention further comprise administering general anesthesia to the patient prior to installation of the pharmaceutical composition comprising the capsaicinoid.

In certain embodiments, the patient experiences attenuation of pain in proximity to the surgical incision site, open wound, or joint for at least about 1 day to about 28 days or more, depending on the dose, with no adverse or lasting effects on wound healing or sensory-motor nerve function. In certain embodiments, the patient experiences attenuation of pain in proximity to the surgical incision site or open wound for about 1 day, about 2 days, about 3 days, about 4 days, about 5 days, about 6 days, about 7 days, about 14 days, or about 21 days, or more.

In certain embodiments, the methods of the invention are associated with a surgical procedure or technique that involves making an incision to the patient. Thus, in certain embodiments, methods of the invention are associated with a median sternotomy, a laparoscopy, a mastectomy, an arthroplasty, cancer surgery, knee surgery, or shoulder surgery, or other type of surgery in a patient. In particular embodiments, the methods of the invention are associated with of bunionectomy, total knee arthoplasty, hernia repair, open cholecystectomy, total hip arthroplasty, or arthroscopic procedures for the shoulder and knee in a patient. Surgical procedures requiring an incision are well known to the clinical practitioner of ordinary skill.

In certain embodiments, the methods of the invention are associated with intra-articular injections to treat or attenuate pain in proximity to a joint where two or more bones make contact. In certain embodiments, the joint is a knee, shoulder, elbow, ankle, hip, or wrist joint. In a particular embodiments, the patient experiences osteoarthritis of the knee, elbow tendonitis, or intermetatarsal neuroma. In other embodiments, the patient undergoes a arthroscopic procedure to the joint.

In certain embodiments, the capsaicinoid administration provides an effect selected from the group consisting of: (a) producing a selective, highly-localized reversible desensitiztion of C-fibers and/or A-delta fibers in a localized area responsible for the initiation of pain for the purpose of reducing or eliminating pain arising from the area, and (b) minimizing potential adverse consequences of C-fiber and/or A-delta activation and or damage outside of the locus of pain.

In certain embodiments, a single instillation of from about 1 μg to 15,000 μg of capsaicin, or a therapeutically equivalent dose of one or more other capsaicinoids, is administered as a formulation to produce a selective, highly-localized reversible desensitization of C-fiber and/or A-delta-fiber in discrete localized areas responsible for the initiation of pain for the purpose of eliminating pain arising from that locus, while minimizing potential adverse consequences of C-fiber and/or A-delta-fiber activation and/or damage outside of the locus of pain. In certain embodiments, from about 600 to about 15,000 micrograms of capsaicin, or a therapeutically equivalent dose of one or more other capsaicinoids, is administered at the surgical site, arthroscopic port, or open wound. In other embodiments, the amount of capsaicin and/or the range of capsaicin administered at the surgical site or open wound is from about 1,000 to about 10,000 micrograms. In other words, the present invention is directed to administration of a single instillation or intra-articular dose of a pharmaceutical composition comprising capsaicin or other capsaicinoid(s) in an amount that is greatly reduced as compared to the dosage range previously considered useful by those skilled in the art to denervate the nerve fibers in a discrete, localized area, without eliciting a systemic effect (e.g., an effect beyond that discrete, localized location). In certain embodiments of the invention, a total dose of about 1000 µg of purified capsaicin is administered as a formulation to a patient undergoing a bunionectomy or hernia repair. In other embodiments, a total dose of about 5,000 µg or about 15,000 µg of purified capsaicin is administered as formulation to a patient undergoing a total knee arthroplasty or total hip arthroplasty. In other embodiments, a total dose of about 3,000 µg of purified capsaicin is administered as a formulation to a patient undergoing open cholecystectomy.

Administration of a single dose of a pharmaceutical composition comprising a capsaicinoid according to the methods of the present invention minimizes and/or prevents systemic delivery of the capsaicin for the purposes of: a) producing a selective, highly-localized reversible densitization of C-fibers and/or A-delta fibers in a discrete, localized area responsible for the initiation of pain (e.g., intra-articular joints, intrabursally) for the purpose of reducing or eliminating pain arising from a discrete locus (i.e., producing antinociception), and b) minimizing potential adverse consequences of C-fiber and/or A-delta activation and or damage outside of the locus of pain (i.e., damage to homeostatic mechanisms, such as cardiac reflex [e.g., Bezold-Jarisch reflex] or micturation reflex [e.g., urge to void] or to nerve fibers in the central nervous system). The analgesic effect provided by the methods of the invention provide pain relief for at least about 48 to about 120 hours, from about 10 to about 21 days, from about 4 to about 5 weeks, and at least about 6 to about 8 weeks, and for at least about 16 weeks or more. Importantly, the methods of the invention provide sustained, reversible analgesia in a patient without adverse effects on wound healing or sensory-motor function.

EXAMPLES

Example 1

Intraoperative Instillation of Capsaicin in a Rat Paw Incision Model

Male Sprague-Dawley rats (Chrales River Laboratories, Inc., Wilimington, Mass., 225-250 g) were anesthetized with 2% isoflurane delivered via nose cone. Ten to 15 minutes before surgery, 100 µL of 2% lidocane was injected in the plantar surface of the right hind paw. A 1 centimeter incision (number 15 scalpel blade) was make through the skin, muscle, and fascia of the anesthetized paw, starting 5 mm from the proximal edge of the heel and extending toward the toes. After elevating the incised tissue, 20 µL of capsaicin formulation or vehicle were instilled into the surgical incision, allowed to dwell for pre-specified times, and then removed via aspiration using a cotton swab. The incision was apposed with 4 single interrupted mattress sutures of 5-0 nylon thread.

Animals were tested on the day before surgery (baseline) and on days 1, 2, 3, and 6 after surgery. Thermal sensitivity was assessed by thermal paw withdrawal latency as described by Hargreaves et al. (Hargreaves et al., *J. Pain* 32:77-88 (1988)). Mechanical hyperalgesia was assessed by the "up-down" algorithm of Chaplan et al. (Chaplan et al., *J. Neurosci. Methods* 53:55-63 (1994)).

As shown in FIG. 1, intraoperative instillation of capsaicin decreased postsurgical thermal hyperalgesia in a rat paw incision model. Animals that received capsaicin formulation instillations lasting 5 or 10 minutes exhibited significantly lower thermal hyperalgesia on post-surgical days 1, 2, and 3 than vehicle- and sham-treated animals. In this study, animals in the active treatment groups received an intraoperative instillation of capsaicin (5 µg per 20 µL 50% PEG-300) for the designated times. Animals in the control groups received 20 µL of 50% PEG-300 for 5 minutes (vehicle) or no intraoperative treatment (sham). Graph points represent mean values; error bars are ±SEM.

Figure 2:
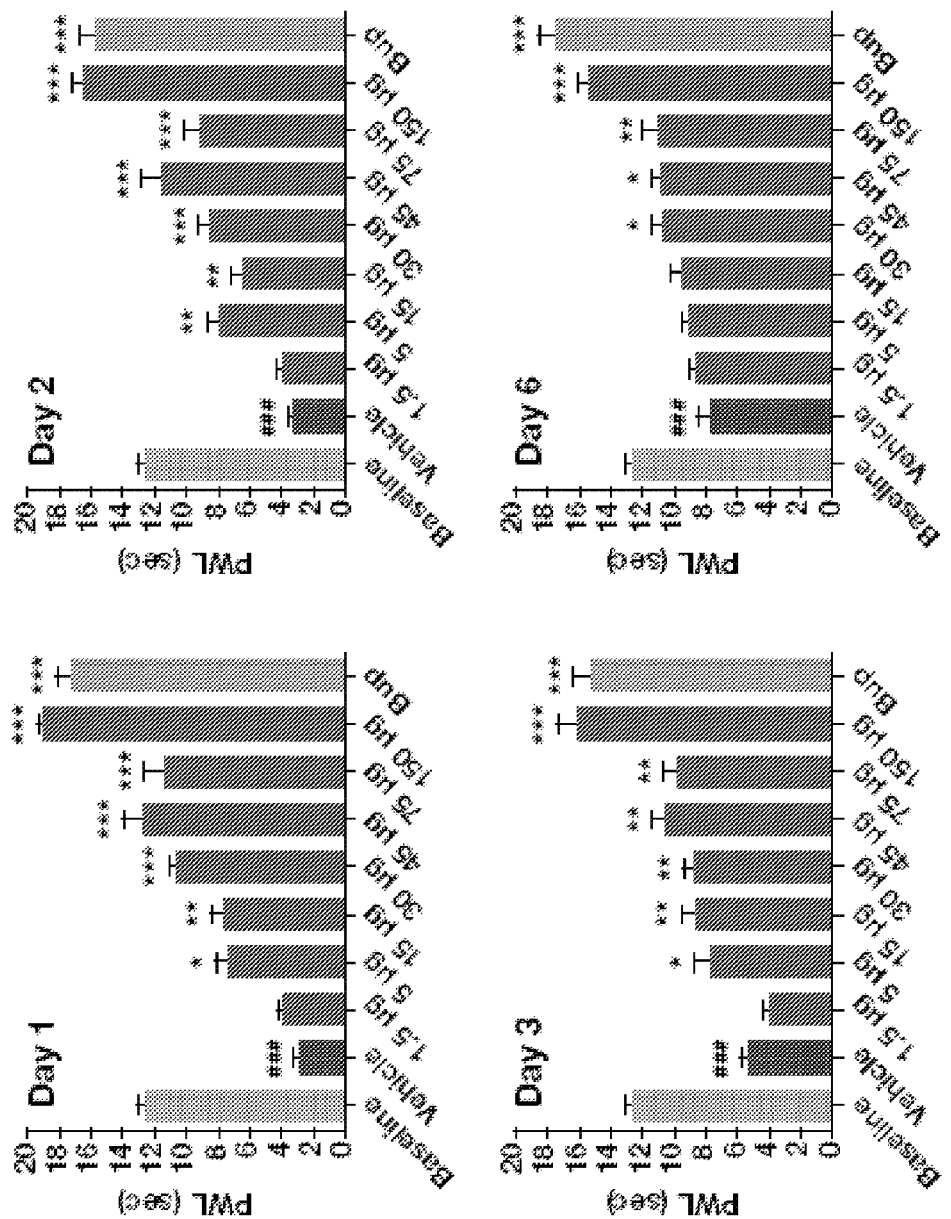
FIG. 2 is four bar graphs showing that intraoperative instillation of capsaicin reduces postsurgical thermal hyperalgesia in a rat paw incision model in a dose-dependent fashion (PWL=paw withdrawal latency).

As shown in FIG. 2, capsaicin-induced reduction of postsurgical thermal hyperalgesia in a rat paw incision model is dose-dependant. Intraoperative instillation of 150 µg of capsaicin produced analgesic effects that were similar to those produced by systemic administration of buprenorphine 1 hour before behavior testing. In the study, animals in the active treatment groups received 5 minute intraoperative instillations of capsaicin formulation (1.5 µg to 150 µg per 20 µL of 50% PEG-300). Animals in the control groups received 5 minute intraoperative instillations of 20 µL of 50% PEG-300 (vehicle) or 5 minute intraoperative instillations of 20 µL of 50% PEG-300 plus subcutaneous buprenorphine (50 µg/kg) 1 hour before behavioral testing (Bup). Bars represent mean values; error bars are ±SEM.

Figure 3:
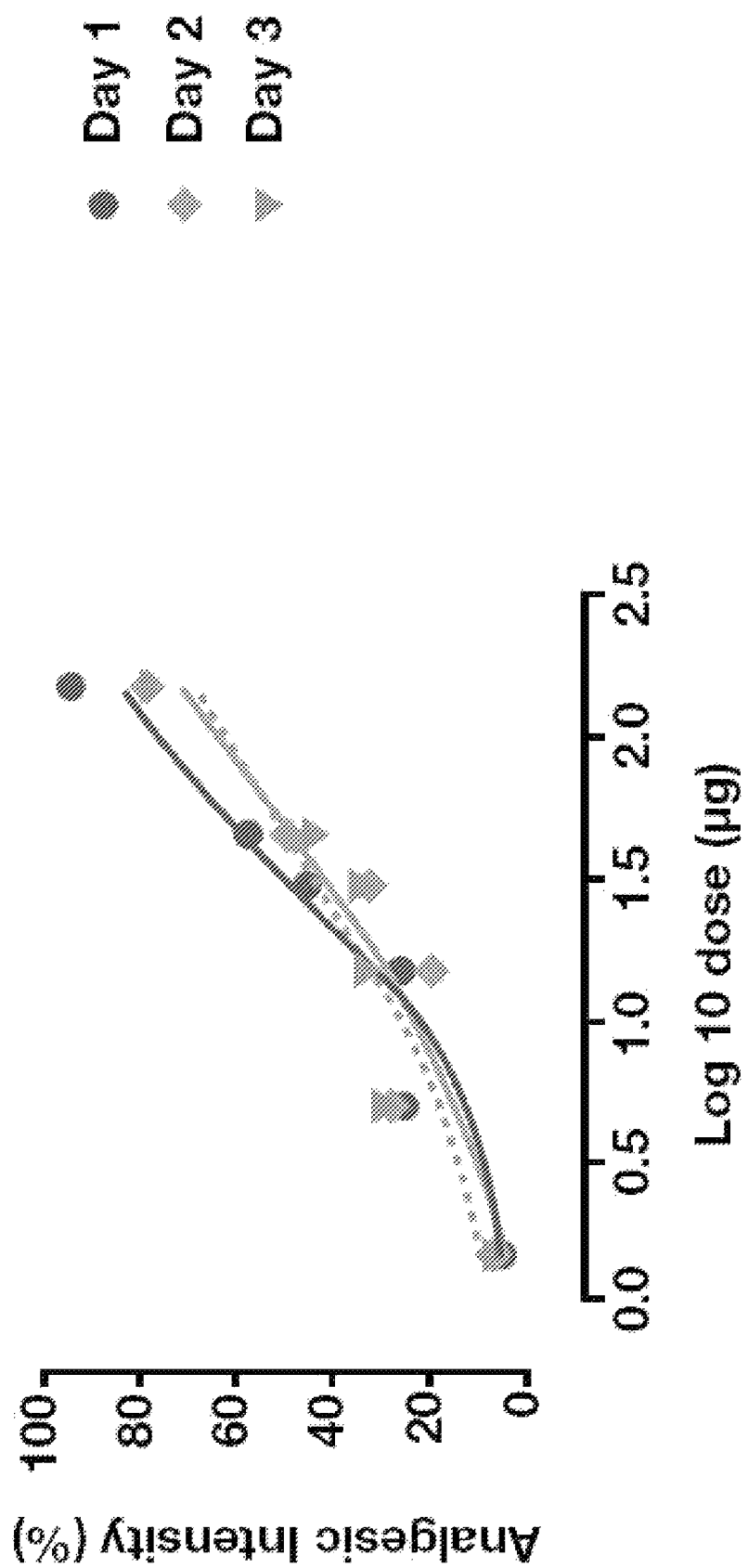
FIG. 3 is a line graph showing the analgesic intensity of capsaicin for postsurgical thermal hyperalgesia in the rat paw incision model.

The experimental data from FIG. 2 were used to calculate analgesic intensity (AI) as follows: $AI(\%)=100\times([PWL_{treat}-PWL_{basal}]/[\text{cut-off}-PWL_{basal}])$, where $PWL_{treat}$ was the paw withdrawal latency after capsaicin treatment, $PWL_{basal}$ was the paw withdrawal latency on day 1 after vehicle treatment, and cut-of was 20 seconds. As shown in FIG. 3 and Table 1, the median effective dose ($ED_{50}$) of capsaicin was 31.01 µg on day 1, 48.53 µg on day 2, and 47.09 µg on day 3. (CI=confidence interval)

TABLE 1

| | $ED_{50}$ (µg) | 95% CI | $ED_{20}$ (µg) | 95% CI | $ED_{10}$ (µg) | 95% CI |
|---|---|---|---|---|---|---|
| Day 1 | 31.01 | 24.59-39.10 | 7.77 | 5.2-11.43 | 3.46 | 1.95-6.12 |
| Day 2 | 48.53 | 35.64-66.08 | 8.38 | 5.32-13.18 | 2.99 | 1.48-6.05 |
| Day 3 | 47.08 | 33.38-66.44 | 6.09 | 3.38-10.96 | 1.84 | 0.74-4.57 |

Figure 4:
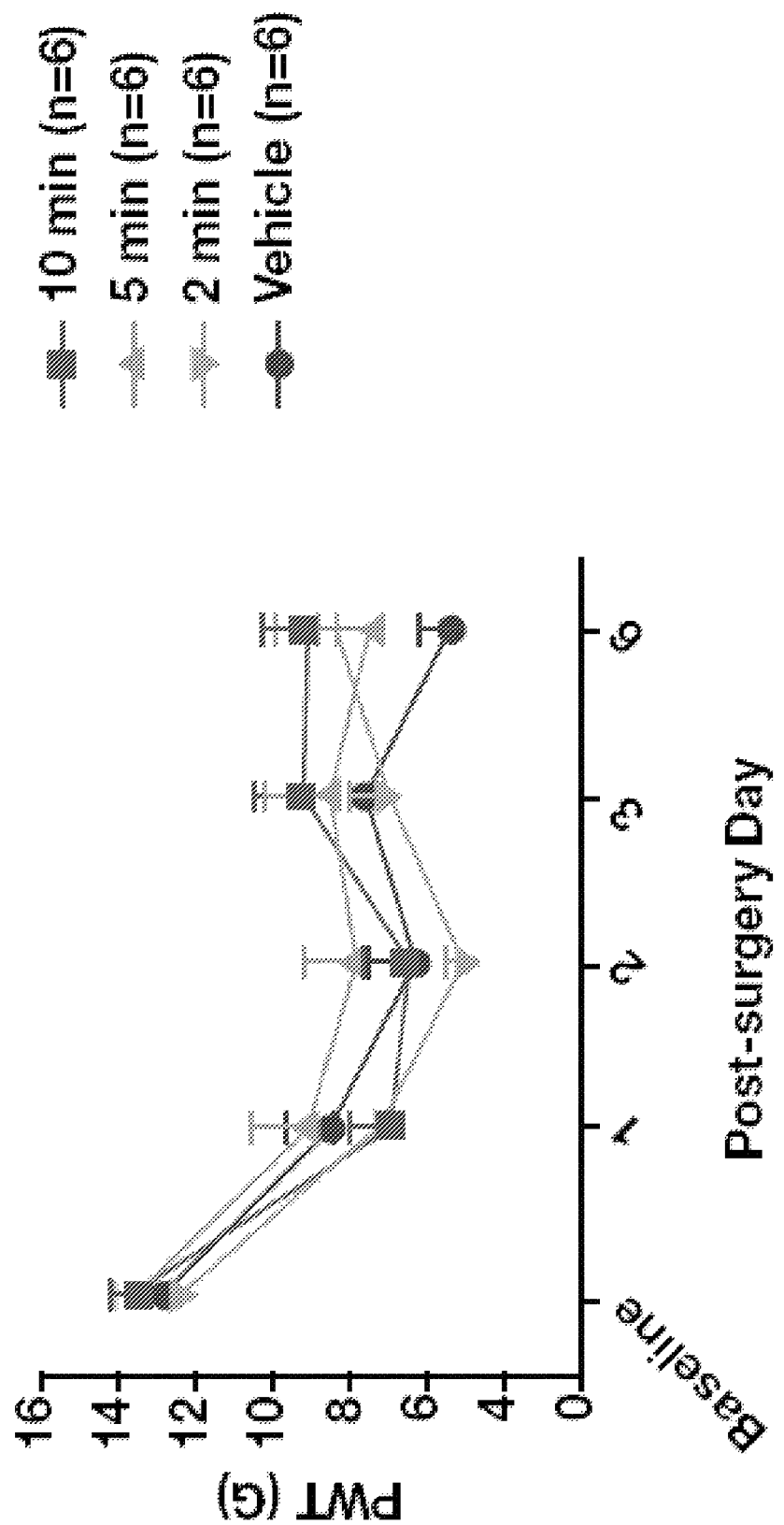
FIG. 4 is a line graph showing that intraoperative instillation of 5 µg of capsaicin does not reduce postsurgical mechanical hyperalgesia in a rat paw incision model (PWT=paw withdrawal threshold).

As shown in FIG. 4, intraoperative instillation of 5 µg capsaicin formulation did not reduce postsurgical mechanical hyperalgesia in a rat paw incision model. In this study, animals in the active treatment groups received an intraoperative instillation of capsaicin (5 µg per 20 µL 50% PEG-300) for the designated times. Animals in the control groups received 20 µL of 50% PEG-300 for 5 minutes (vehicle). Graph points represent mean values; error bars are ±SEM.

Figure 5:
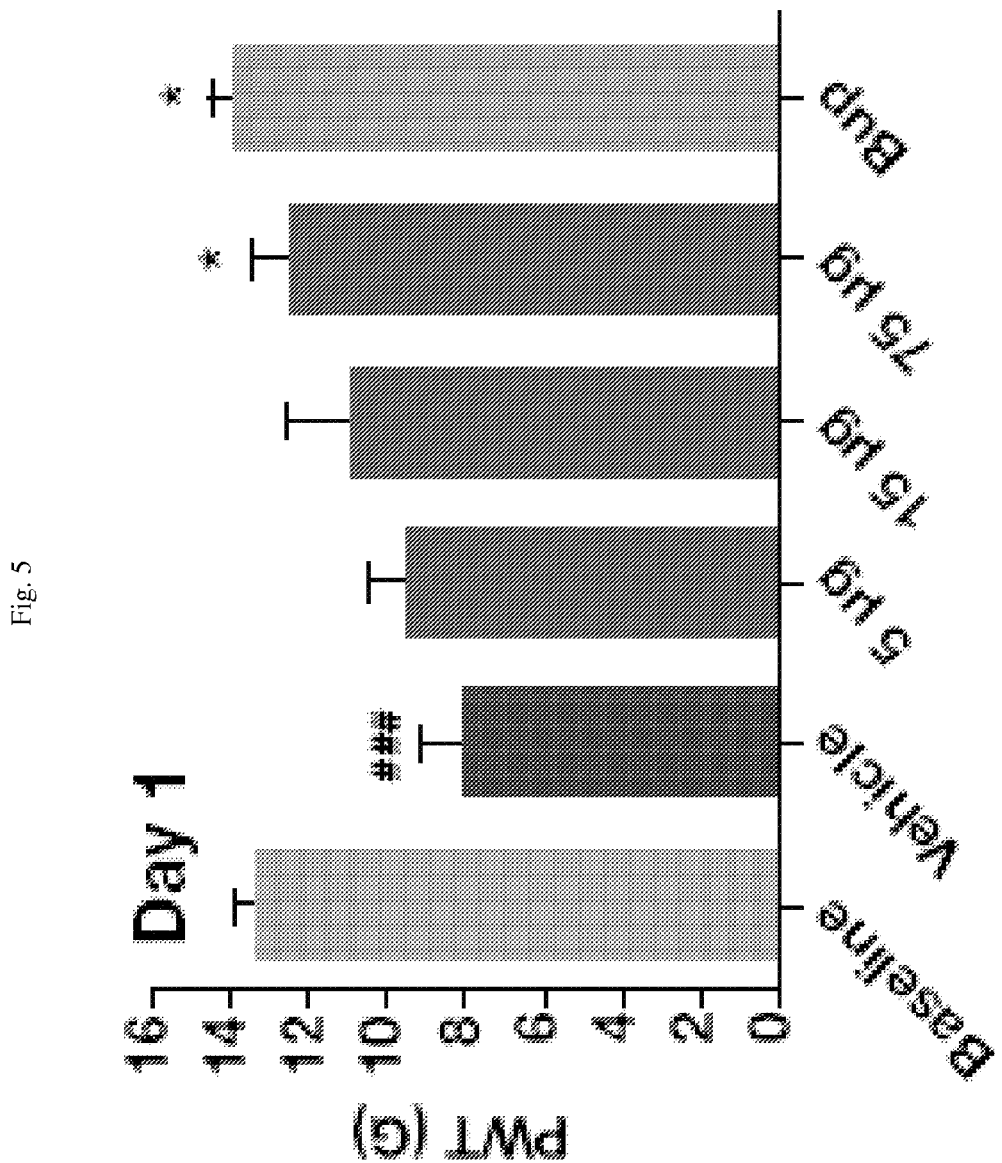
FIG. 5 is a bar graph showing that intraoperative instillation of 75 µg of capsaicin reduces postsurgical mechanical hyperalgesia in a rat paw incision model (PWT=paw withdrawal threshold).

As shown in FIG. 5, capsaicin-induced reduction of postsurgical mechanical hyperalgesia in a rat paw incision model is dose-dependant. Intraoperative instillation of 75 µg of capsaicin formulation produced significant analgesic effects relative to vehicle. In this study, animals in the active treatment groups received 5 minute intraoperative instillations of capsaicin (5, 15, or 75 µg per 20 µL of 50% PEG-300). Animals in the control groups received 5 minute intraoperative instillations of 20 µL of 50% PEG-300 (vehicle) or subcutaneous injection of buprenorphine (50 µg/kg) 1 hour before behavioral testing (Bup). Bars represent mean values; error bars are ±SEM.

Figure 6:
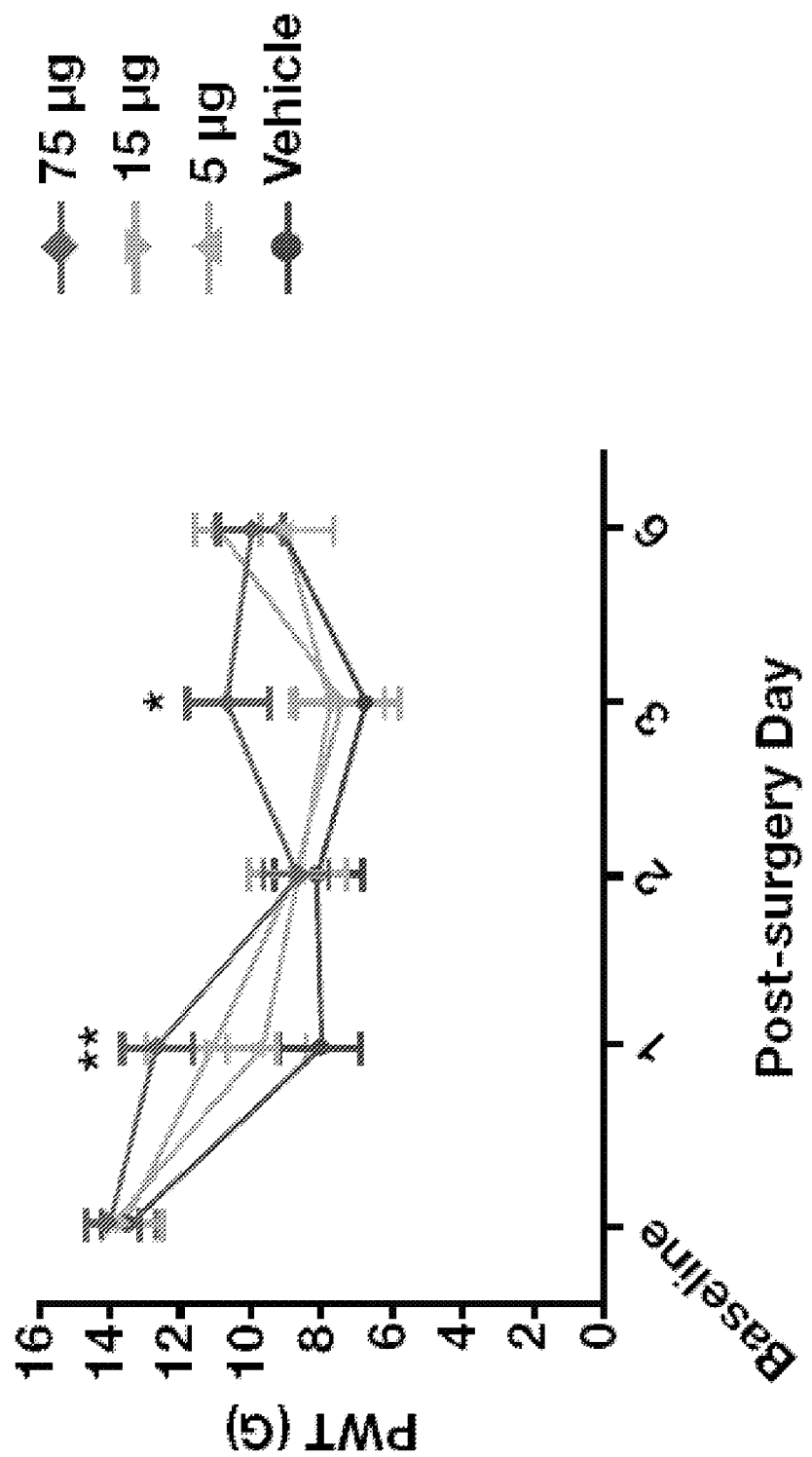
FIG. 6 is a line graph showing that intraoperative instillation of 75 µg of capsaicin reduces postsurgical mechanical hyperalgesia in a rat paw incision model on days 1 and 3. (PWT=paw withdrawal threshold).

As shown in FIG. 6, reduction of postsurgical mechanical hyperalgesia was greater after an instillation of 75 µg capsaicin formulation than vehicle on days 1 and 3. In this study, animals in the active treatment groups received 5 minute intraoperative instillations of capsaicin (5, 15, or 75 µg per 20 µL of 50% PEG-300). Animals in the control groups received 5 minute intraoperative instillations of 20 µL of 50% PEG-300 (vehicle). Graph points represent mean values; error bars are ±SEM.

In summary, intraoperative instillation of capsaicin produced a sustained analgesia lasting up to 6 days in a rat paw incision model, with higher potency against postsurgical thermal hyperalgesia than mechanical hyperalgesia. These data indicate that capsaicin may effect thermal nociceptors (unmyelinated C-fibers) more specifically than mechanical receptors (A-δ fibers).

Example 2

Single Instillation Administration of Capsaicin Has No Adverse Effect on Rat Bone and Soft Tissue Wound Healing or Sensory-Motor Function Adult CD Charles River rats were anesthetized with isoflurane and oxygen. Extrafascicular instillation: The sciatic nerve was exposed by blunt dissection and 100 µl of test article was applied directly to the sciatic nerve). Treatment groups received either vehicle (25% PEG 300), 0.0083 mg capsaicin (≧98% pure) or 0.025 mg capsaicin dissolved in vehicle. A sham group underwent the same surgical procedure but did not receive any test article. Osteotomy: The lateral aspect of the right femur was exposed and cut at the midshaft using an oscillating saw. An intramedullary Kirshner wire was inserted for fracture reduction and the osteotomy site irrigated with 100 µl of the vehicle (20% PEG 300, 10 mM histidine and 5% (w/v) sucrose) or 0.5 mg capsaicin diluted in vehicle.

Behavioral testing: Individual rats were placed in a black plexiglass observation box and parameters including posture, rearing, vocalization, bizarre behavior, mobility, and stereotypy were evaluated based on the methods of Moser et al. (Moser et al., *Fundam. Appl. Toxicol.* 11: 189-206 (1988)). Forelimb and hindlimb grip strength was measured using a strain gauge that recorded the maximum force in Kg as described by Meyer (Meyer et al. *Neurobehav. Toxicol.* 1:233-236 (1979) and Meyer and Ross (1966) U.S. Environmental Protection Agency, Wasington, D.C.) Hindlimb splay was quantitatively measured as described by Edwards et al. (Edwards et al., *Toxicol Appl. Pharmacol.* 40:589-591 (1977)). Thermal response was measured using the hot plate test as previously described by Ankier (Aniker *Eur. J. Pharmacol.* 27:1-4 (1974). The hot plate was set at 52° C. and the latency between placement of the animal on the heated surface and the first paw lick was recorded. The test was administered three times at predose and at days 3, 14 and 28 post-surgery and the values averaged.

Histology: Rats were euthanized by intraperitoneal injection of sodium pentobarbital (90 mg/Kg) followed by transcardiac perfusion with 0.9% saline then 3% paraformaldehyde and 3% glutaraldehyde in 0.1 M phosphate buffer. The entire length of sciatic nerve was embedded in paraffin or plastic and representative sections were taken from the treatment site and proximal and distal sites and stained with hematoxylin and eosin (H&E). Sections were scored for neuronal and myelin integrity, appearance and inflammation.

Biomechanical Testing: Both osteotomized and contralateral whole femurs were tested in 4-point bending with a servohydrolic material test system (858 Mini Bionix) to determine the material properties of the cortical bone. Peak load, energy to break (area under the curve) and stiffness were derived. Peak load was measured as the maximum height of the load-displacement curve, and stiffness was measured as the slope of the linear portion of the load-displacement curve.

Statistics: Levene's test was used to assess homogeneity of group variances for each specified end point and for each data collection interval. If Levene's test was not significant (P>0.01), a pooled estimate of the variance (Means Square Error) was computed from a one-way analysis of variance (ANOVA) and utilized by Dunnett's comparison of each treatment group with the control group. If Levene's test was significant (P<0.01), comparisons with the control group were made using Welch's t-test with a Bonferroni correction.

Figure 7:
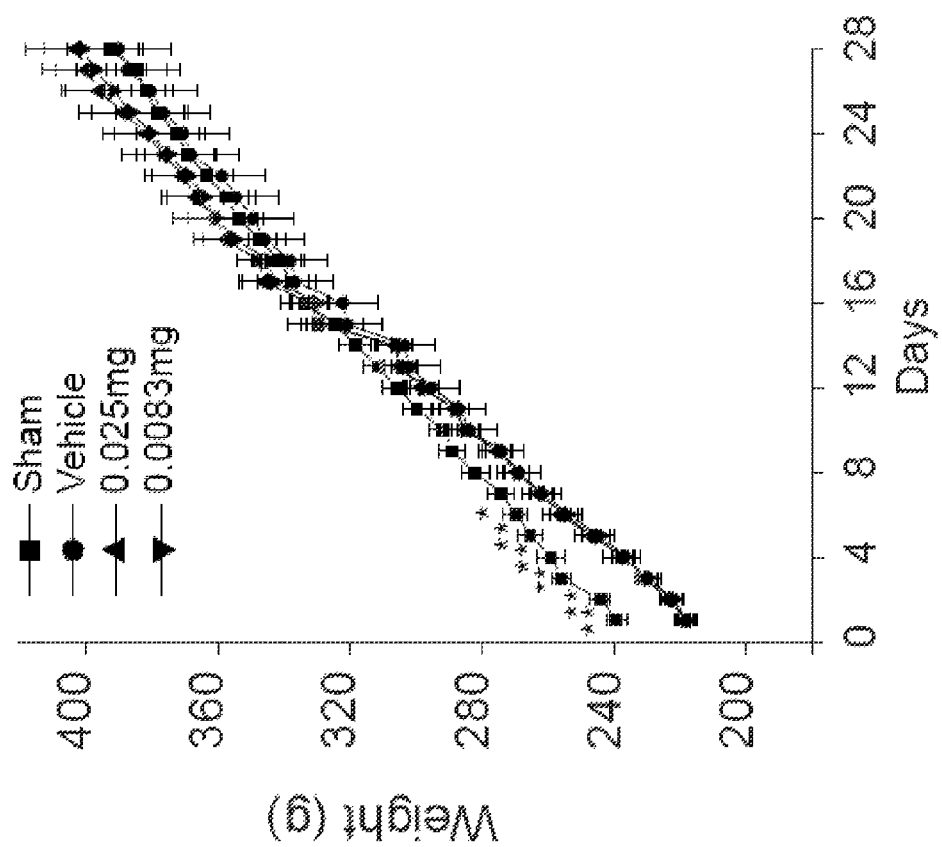
FIG. 7 is a graph showing extrafascicular treatment (instillation) with capsaicin reduces weight gain over the first 10 post-operative days compared to sham-operated rats.

As shown in FIG. 7, is a graph showing extrafascicular instillation with capsaicin reduces weight gain over the first 10 post-operative days compared to sham-operated rats.

Figure 8:
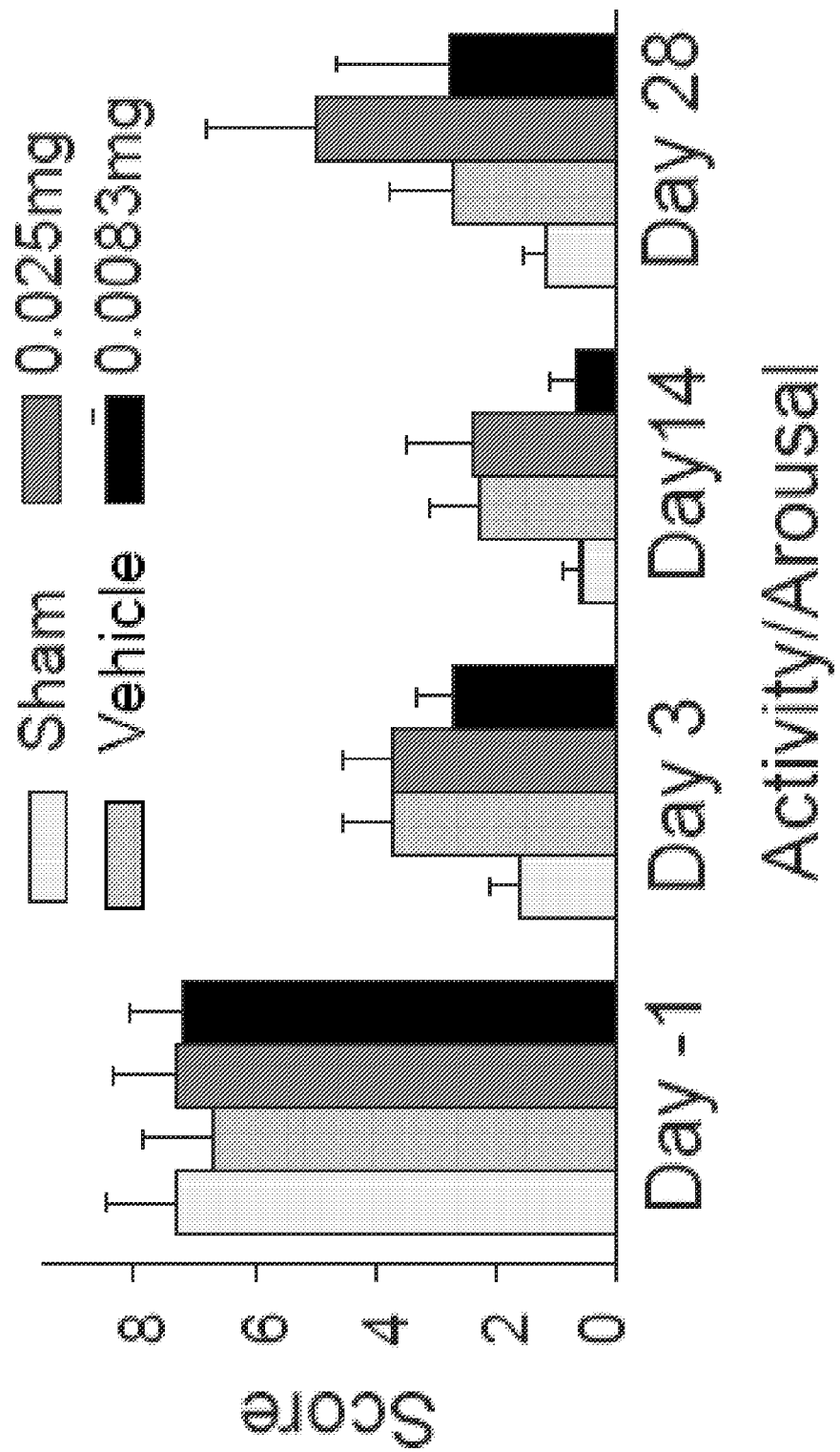
FIG. 8 is a bar graph showing extrafascicular treatment (instillation) with capsaicin does not effect activity/arousal in rats.

As shown in FIG. 8, extrafascicular instillation with capsaicin does not effect activity/arousal in rats.

Figure 9:
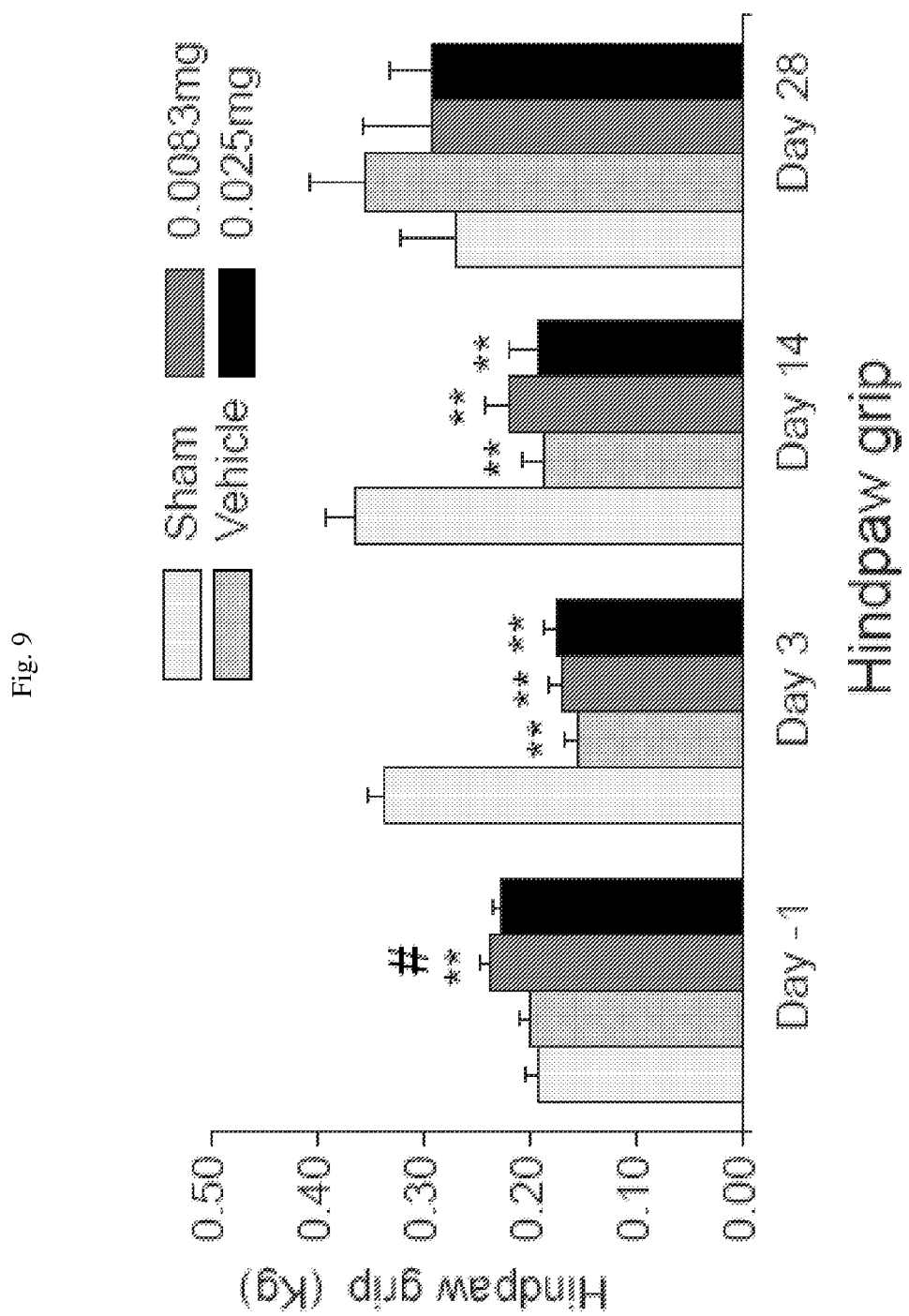
FIG. 9 is a bar graph showing extrafascicular treatment (instillation) with capsaicin decreases hindpaw grip strength on post operative days 3 and 14 in rat.

As shown in FIG. 9, extrafascicular instillation with capsaicin decreases hindpaw grip strength on post operative days 3 and 14 in rat.

Figure 10:
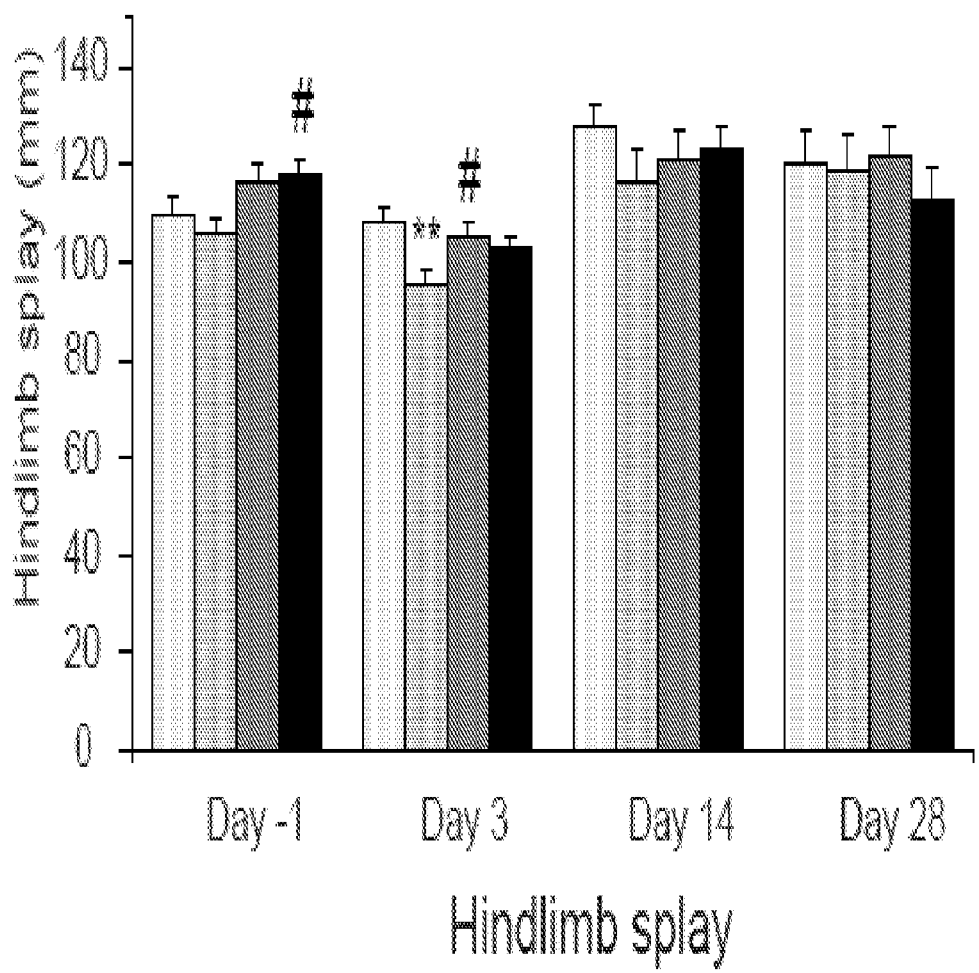
FIG. 10 is bar graph showing extrafascicular treatment (instillation) with capsaicin has no effect on hindpaw splay in rat.

As shown in FIG. 10, extrafascicular instillation with capsaicin has no effect on hindpaw splay in rat.

Figure 11:
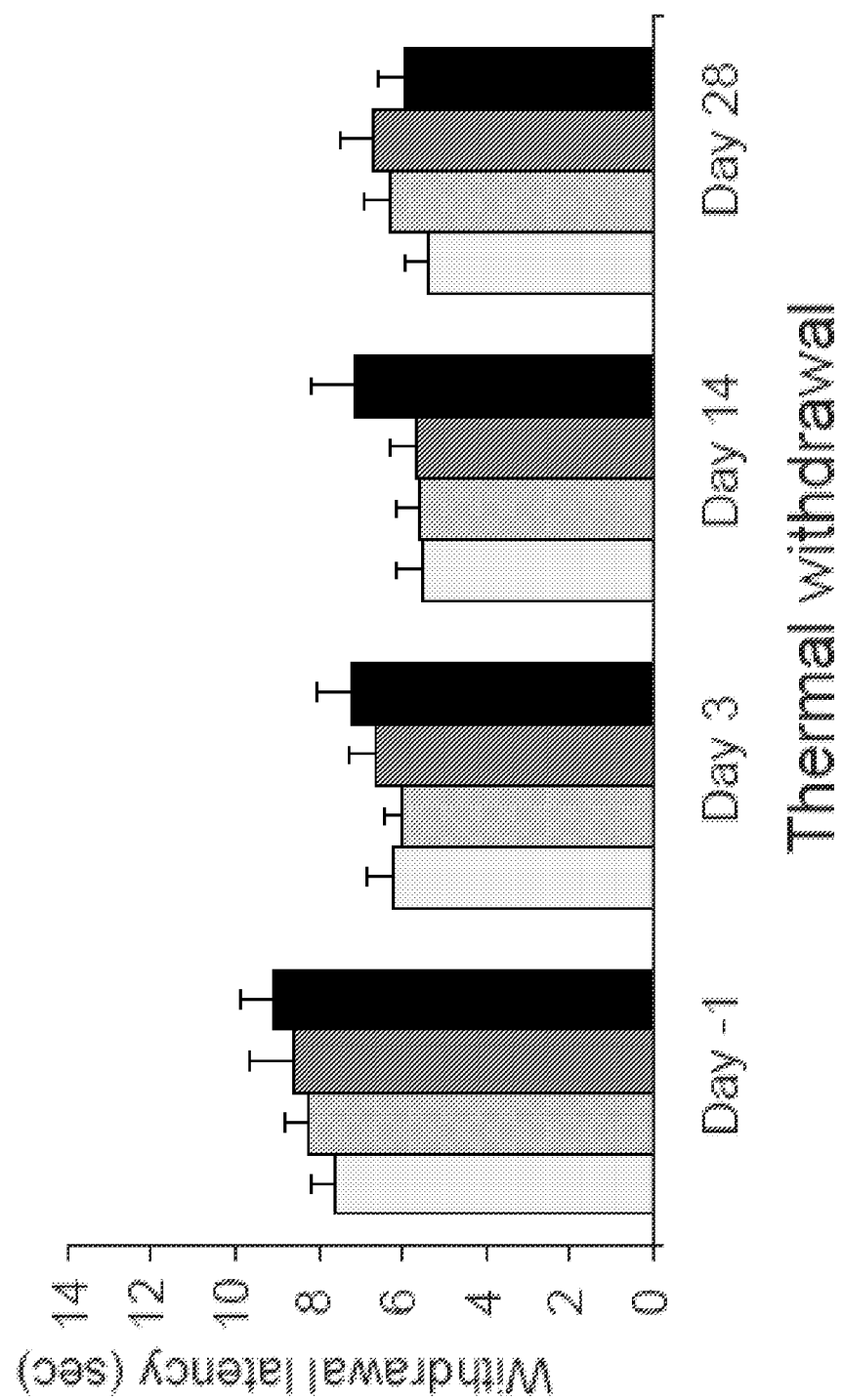
FIG. 11 is a bar graph showing extrafascicular treatment (instillation) with capsaicin has no effect on thermal withdrawal in rat
Figure 12:
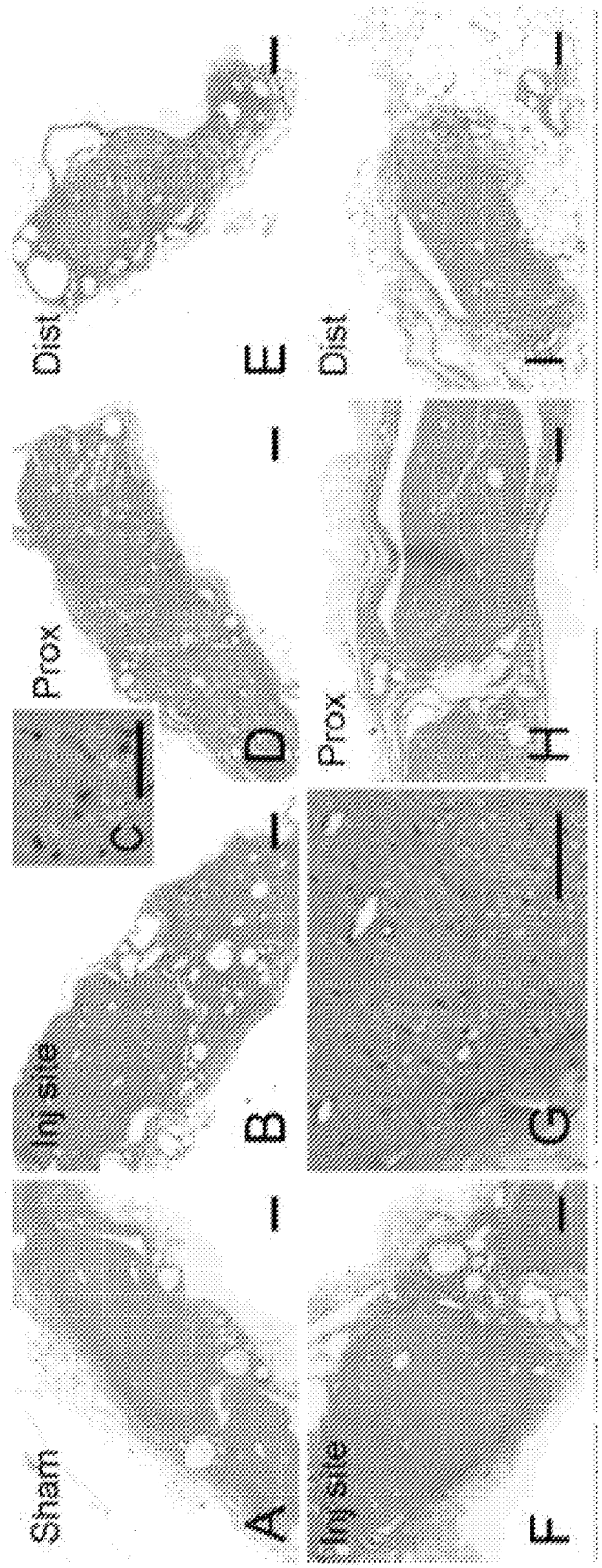
FIG. 12 is a series of photographs with panels A-I showing hematoxylin and eosin stained sections of sciatic nerve from extrafascicular treatment (instillation) with capsaicin (0.025 mg) in rat. Three days (B-E, C is high magnification of B) or 28 days (F-I) post treatment there is no difference in appearance between sham operated (A) and treated animals.

As shown in FIG. 11, extrafascicular instillation with capsaicin has no effect on thermal withdrawal in rat As shown in FIG. 12, hematoxylin and eosin stained sections of sciatic nerve from extrafascicular instillation with capsaicin (0.025 mg) in rat show no differences in appearance 3 days (B-E, C is high magnification of B) or 28 days (F-I) post treatment between sham operated (A) and treated animals.

Figure 13:
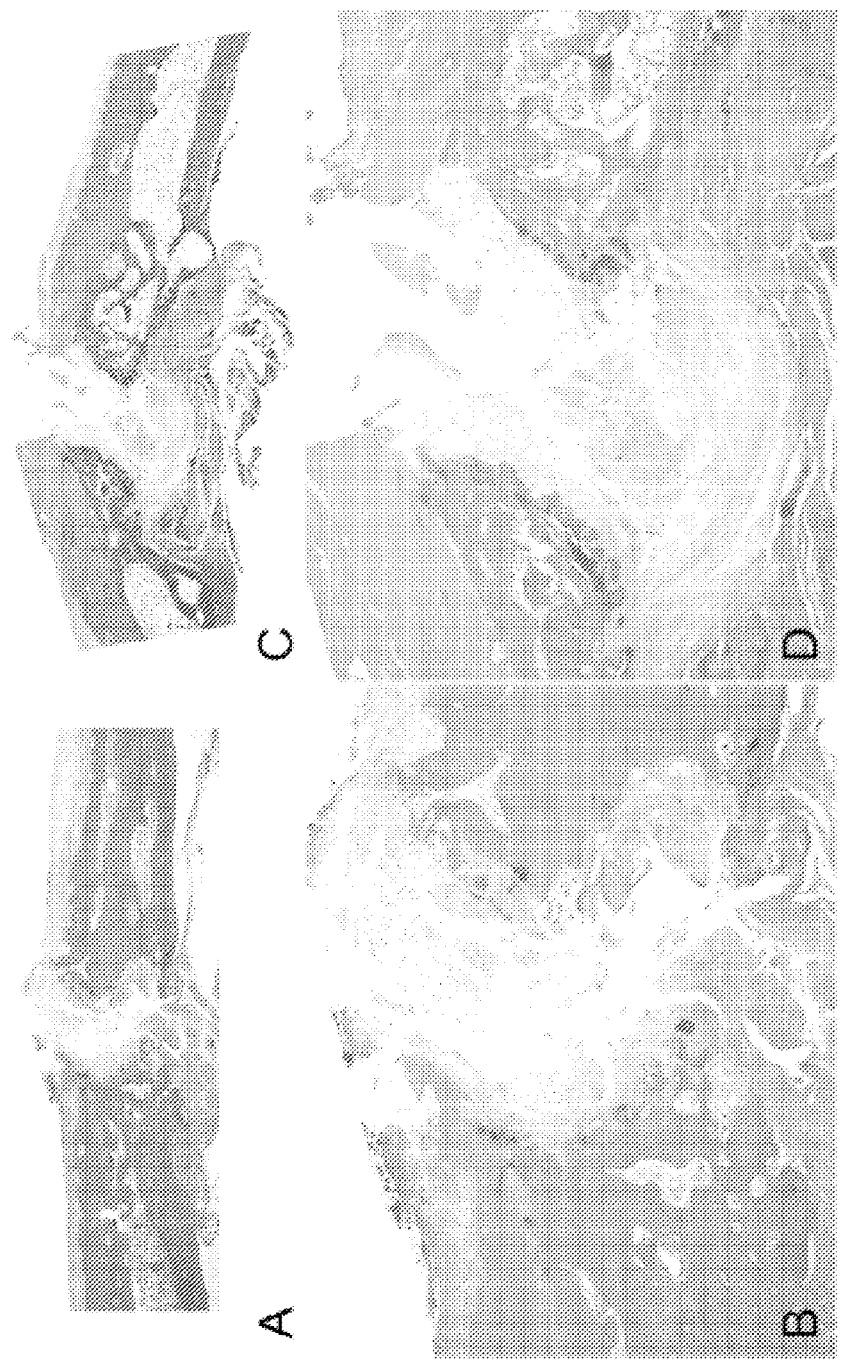
FIG. 13 is a series of photographs with panels A-D showing hematoxylin and eosin stained sections of an osteotomy site from vehicle (A and B) and 0.5 mg capsaicin (C and D) treated femors.

As shown in FIG. 13, hematoxylin and eosin stained sections of an osteotomy site from vehicle (A and B) and 0.5 mg capsaicin (C and D) treated femors show no differences.

Figure 14:
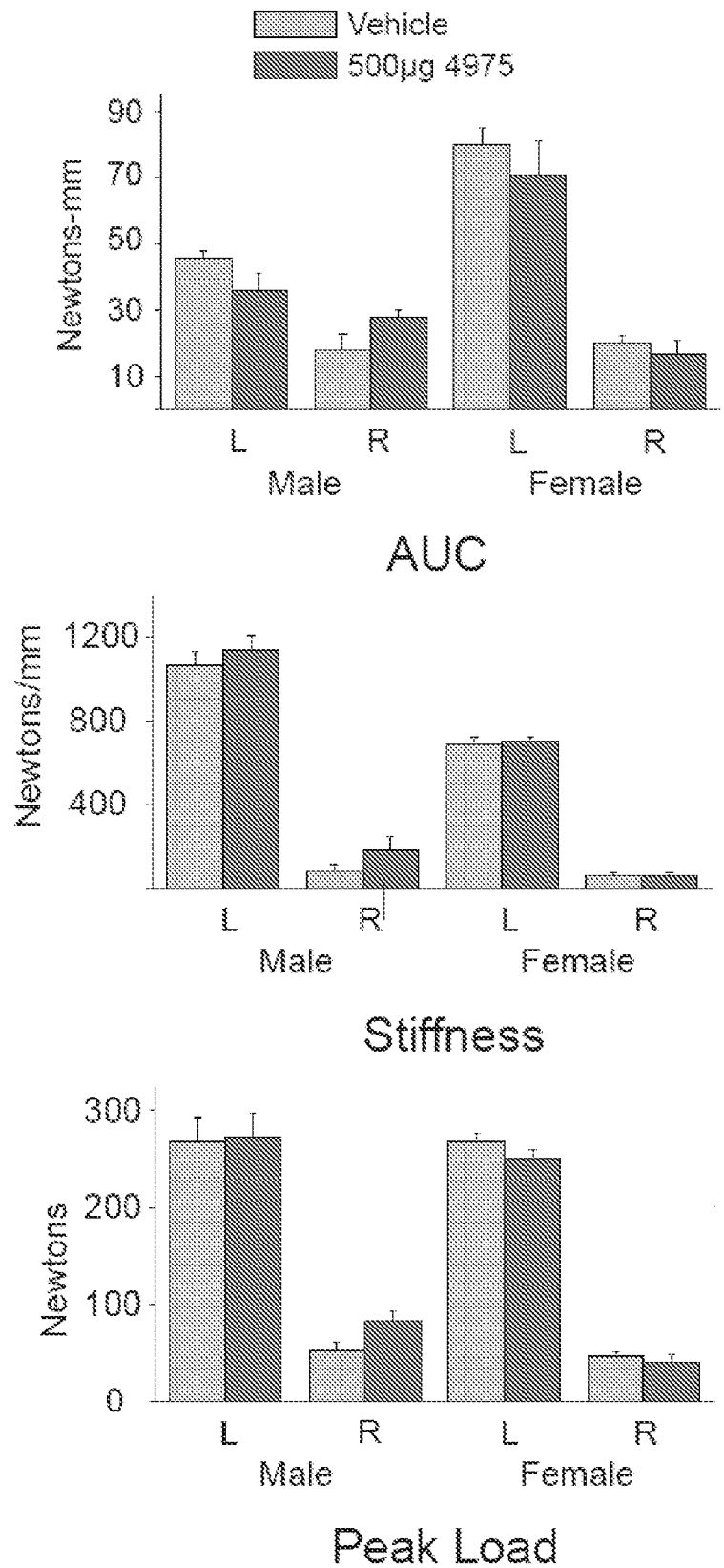
FIG. 14 is a series of three bar graphs showing that there is no difference between vehicle and capsaicin-treated right femors.

As shown in FIG. 14, there is no difference between vehicle and capsaicin-treated right femors in terms of general integrity of bone structure (AUC), stiffness, or peak load.

In summary, extrafascicular instillation of capsaicin has no observable adverse effects on wound and bone healing following osteotomy or on the structural integrity of exposed nerve.

The present invention has been described with reference to certain embodiments thereof. However, the scope of the invention is not limited to the embodiments described or exemplified. Workers of ordinary skill in the relevant arts will readily appreciate that other embodiments and examples can be practiced without departing from the scope of the present invention. All such variations are considered to be part of, and therefore encompassed by, the present invention.

All publications, patent applications, patents, and other references mentioned herein are incorporated by reference in their entirety.

What is claimed is:

1. A method for attenuating pain in proximity to an open wound, arthroscopic port, or surgical incision in a patient comprising:
    (a) instilling a therapeutically effective amount of a pharmaceutical composition comprising a capsaicinoid into said open wound, arthroscopic port, or surgical incision;
    (b) allowing said pharmaceutical composition to dwell for about 2 minutes to about 10 minutes; and
    (c) aspirating said open wound, arthroscopic port, surgical incision to remove said pharmaceutical composition.

2. The method of claim 1 further comprising closing said open wound or surgical incision.

3. A method for attenuating pain in proximity to a joint in a patient comprising:
    (a) intra-articularly injecting a therapeutically effective amount of a pharmaceutical composition comprising a capsaicinoid into said joint;
    (b) allowing said pharmaceutical composition to dwell for about 2 minutes to about 10 minutes; and
    (c) aspirating said joint to remove said pharmaceutical composition.

4. The method of claim 1 or 3, wherein said therapeutically effective amount of said capsaicinoid is about 10 µg to about 15,000 µg.

5. The method of claim 3, wherein said therapeutically effective amount of said capsaicinoid is about 100 µg to about 1,000 µg.

6. The method of claim 5, wherein said therapeutically effective amount of said capsaicinoid is about 1000 µg.

7. The method of claim 1 or 3, wherein said pharmaceutical composition is administered in a volume of about 0.1 ml to about 1000 ml.

8. The method of claim 7, wherein said pharmaceutical composition comprises polyethylene glycol and water.

9. The method of claim 8, wherein said pharmaceutical composition comprises about 25% PEG 300 in water.

10. The method of claim 1 or 3 further comprising co-administering one or more additional therapeutic agents to said patient.

11. The method of claim 10, wherein said one or more additional therapeutic agents comprises a local anesthetic, wherein said local anesthetic is administered to said patient prior to or concurrently with said pharmaceutical composition in an amount and location effective to attenuate an initial hyperalgesic effect of said pharmaceutical composition.

12. The method of claim 11, wherein said local anesthetic is lidocaine.

13. The method of claim 1 or 3, further comprising administering general anesthesia to said patient prior to said instillation of said pharmaceutical composition.

14. The method of claim 1 or 3, wherein said patient experiences attenuation of pain in proximity to said open wound, said surgical incision site, or said joint for at least about 48 hours.

15. The method of claim 14, wherein said patient experiences attenuation of pain for at least about one week.

16. The method of claim 1 or 3, wherein said patient experiences no adverse effect on wound healing or sensory-motor nerve function.

17. The method of claim 1 or 3, wherein said pharmaceutical composition comprising a capsaicinoid causes reversible desensitization of C-fibers.

18. The method of claim 1, wherein said surgical incision is associated with a surgical procedure selected from the group consisting of bunionectomy, total knee arthroplasty, hernia repair, open cholecystectomy, total hip arthroplasty, and arthroscopic procedure.

19. The method of claim 3, wherein said joint is selected from the group consisting of knee, shoulder, elbow, ankle, hip, and wrist.

20. The method of claim 1 or 3, wherein said capsaicinoid is capsaicin.

21. The method of claim 19, wherein said capsaicin is purified capsaicin.

22. The method of claim 21, wherein said capsaicin is greater than 99% pure.

23. A method for attenuating pain in proximity to a surgical incision in a patient comprising:
    (a) instilling a pharmaceutical composition comprising about 1000 µg to about 15,000 µg of purified capsaicin into said surgical incision;
    (b) allowing said pharmaceutical composition to dwell for about 2 minutes to about 10 minutes; and
    (c) aspirating said surgical incision to remove said pharmaceutical composition.

24. The method of claim 23, wherein said surgical incision is associated with a bunionectomy, total knee arthroplasty, hernia repair, open cholecystectomy, total hip arthroplasty, and arthroscopic procedure.

25. A method of attenuating pain in proximity to joint in a patient comprising:
    (a) intra-articularly injecting a pharmaceutical composition comprising about 100 µg to about 1000 µg of purified capsaicin into said joint;
    (b) allowing said pharmaceutical composition to dwell for about 2 minutes to about 10 minutes; and
    (c) aspirating said joint to remove said pharmaceutical composition.

26. The method of claim 24, wherein said joint is a knee joint and said pain is caused by osteoarthritis.

27. The method of claim 25, wherein said pain is caused by an arthroscopic procedure.

* * * * *